(12) United States Patent
Arnott et al.

(10) Patent No.: US 10,182,969 B2
(45) Date of Patent: Jan. 22, 2019

(54) ASEPTIC PIERCING SYSTEM AND METHOD

(71) Applicant: Regeneron Pharmaceuticals, Inc., Tarrytown, NY (US)

(72) Inventors: Rachel Paige Arnott, Loudonville, NY (US); Bart E. Burgess, Glenmont, NY (US); Michael Cupicha, East Schodack, NY (US); Alexei Goraltchouk, Cambridge, MA (US); Bryan Grygus, Cohoes, NY (US); Mike Stelmah, Tarrytown, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 490 days.

(21) Appl. No.: 15/066,791

(22) Filed: Mar. 10, 2016

(65) Prior Publication Data

US 2016/0262984 A1 Sep. 15, 2016

Related U.S. Application Data

(60) Provisional application No. 62/130,718, filed on Mar. 10, 2015.

(51) Int. Cl.
*A61J 1/20* (2006.01)
*A61J 1/14* (2006.01)
(Continued)

(52) U.S. Cl.
CPC .......... *A61J 1/2096* (2013.01); *A61J 1/1406* (2013.01); *A61J 1/1443* (2013.01); *A61J 1/201* (2015.05);
(Continued)

(58) Field of Classification Search
CPC ........ A61J 1/2096; A61J 1/201; A61J 1/2048; A61J 1/2072; A61J 1/1406; A61J 1/1443;
(Continued)

(56) References Cited

U.S. PATENT DOCUMENTS 2,459,304 A  1/1949 Blank
3,340,671 A  9/1967 Loo
(Continued)

FOREIGN PATENT DOCUMENTS

AU  2002301321 B2  2/2003
EP  1064035 B1  11/2003
(Continued)

OTHER PUBLICATIONS

International Search Report and Written Opinion issued in application No. PCT/US2016/021790 dated Jun. 24, 2016.
(Continued)

*Primary Examiner* — Philip R Wiest
(74) *Attorney, Agent, or Firm* — Bookoff McAndrews, PLLC

(57) ABSTRACT

The present disclosure provides aseptic vial piercing and sterilization systems, and methods of assembling, using and sterilizing same. The systems and methods utilize a pre-sterilized primary container including a first end, a first cavity, a second end with an opening in communication with the first cavity, a septum at least partially sealing the opening, and a product within the first cavity. The systems and methods include an injection assembly including a first end portion of a hollow flowpath forming member. The injection assembly and the primary container may be assembled in a non-sterile environment to form a second cavity extending about the first end portion of the flowpath forming member and to the primary container. The second cavity may then be selectively sterilized in a non-deleterious
(Continued)

manner to the product to allow the first end portion to aseptically pierce the septum to extend into the first cavity.

22 Claims, 21 Drawing Sheets

(51) Int. Cl.
*A61L 2/18* (2006.01)
*A61M 5/315* (2006.01)
*A61M 39/18* (2006.01)
*A61M 5/24* (2006.01)
*A61M 5/31* (2006.01)

(52) U.S. Cl.
CPC ............ *A61J 1/2048* (2015.05); *A61J 1/2072* (2015.05); *A61L 2/18* (2013.01); *A61M 5/2459* (2013.01); *A61M 5/31511* (2013.01); *A61L 2202/23* (2013.01); *A61M 39/18* (2013.01); *A61M 2005/247* (2013.01); *A61M 2005/2474* (2013.01); *A61M 2005/3118* (2013.01); *A61M 2005/31518* (2013.01)

(58) Field of Classification Search
CPC ........ A61J 2/18; A61J 5/2459; A61J 5/31511; A61J 2005/247; A61J 2005/2474; A61J 2005/3118; A61J 2005/31518
USPC .................................. 604/403–414
See application file for complete search history.

(56) References Cited

U.S. PATENT DOCUMENTS

| | | |
|---|---|---|
| 3,872,992 A | 3/1975 | Larson |
| 3,916,894 A | 11/1975 | Cloyd |
| 4,187,861 A | 2/1980 | Heffernan |
| 4,244,287 A | 1/1981 | Maffet |
| 4,396,385 A | 8/1983 | Kelly et al. |
| 4,410,323 A | 10/1983 | Hodosh et al. |
| 4,548,601 A | 10/1985 | Lary |
| 4,624,660 A | 11/1986 | Mijers et al. |
| 4,703,781 A | 11/1987 | Meyer et al. |
| 5,073,169 A | 12/1991 | Raiken |
| 5,088,996 A | 2/1992 | Kopfer et al. |
| 5,322,515 A | 6/1994 | Karas et al. |
| 5,334,179 A | 8/1994 | Poli et al. |
| 5,354,287 A | 10/1994 | Wacks |
| 5,466,220 A | 11/1995 | Brenneman |
| 5,514,116 A | 5/1996 | Vaillancourt et al. |
| 5,858,001 A | 1/1999 | Tsals et al. |
| 5,873,860 A | 2/1999 | Kahlert |
| 6,003,566 A | 12/1999 | Thibault et al. |
| 6,003,736 A | 12/1999 | Ljunggren |
| 6,022,339 A * | 2/2000 | Fowles .................. A61J 1/10 604/411 |
| 6,074,369 A | 6/2000 | Sage et al. |
| 6,090,070 A | 7/2000 | Hager et al. |
| 6,149,614 A | 11/2000 | Dunshee et al. |
| 6,171,276 B1 | 1/2001 | Lippe et al. |
| 6,189,580 B1 | 2/2001 | Thibault et al. |
| 6,277,095 B1 | 8/2001 | Kriesel et al. |
| 6,364,865 B1 | 4/2002 | Lavi et al. |
| 6,378,576 B2 | 4/2002 | Thibault et al. |
| 6,478,771 B1 | 11/2002 | Lavi et al. |
| 6,500,150 B1 | 12/2002 | Gross et al. |
| 6,547,755 B1 | 4/2003 | Lippe et al. |
| 6,585,693 B1 | 7/2003 | Dischler |
| 6,595,956 B1 | 7/2003 | Gross et al. |
| 6,641,565 B1 | 11/2003 | Lavi et al. |
| 6,645,181 B1 | 11/2003 | Lavi et al. |
| 6,681,946 B1 | 1/2004 | Jansen et al. |
| 6,689,108 B2 | 2/2004 | Lavi et al. |
| 6,723,068 B2 | 4/2004 | Lavi et al. |
| 6,799,612 B2 | 10/2004 | Stewart et al. |
| 6,824,529 B2 | 11/2004 | Gross et al. |
| 6,837,876 B2 | 1/2005 | Bally et al. |
| 6,843,782 B2 | 1/2005 | Gross et al. |
| 6,939,324 B2 | 9/2005 | Gonnelli et al. |
| 6,945,417 B2 | 9/2005 | Jansen et al. |
| 7,250,037 B2 | 7/2007 | Shermer et al. |
| 7,294,752 B1 | 11/2007 | Propp |
| 7,384,413 B2 | 6/2008 | Gross et al. |
| 7,416,540 B2 | 8/2008 | Edwards et al. |
| 7,455,663 B2 | 11/2008 | Bikovsky |
| 7,481,792 B2 | 1/2009 | Gonnelli et al. |
| 7,563,253 B2 | 7/2009 | Tanner et al. |
| D602,155 S | 10/2009 | Foley et al. |
| D602,586 S | 10/2009 | Foley et al. |
| 7,628,770 B2 | 12/2009 | Ethelfeld et al. |
| 7,648,482 B2 | 1/2010 | Edwards et al. |
| 7,648,483 B2 | 1/2010 | Edwards et al. |
| 7,674,246 B2 | 3/2010 | Gillespie et al. |
| 7,678,072 B2 | 3/2010 | Weber |
| 7,678,079 B2 | 3/2010 | Shermer et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,780,636 B2 | 8/2010 | Radmer et al. |
| 7,883,660 B2 | 2/2011 | Matsuda et al. |
| 7,909,796 B2 | 3/2011 | Weber |
| 7,918,823 B2 | 4/2011 | Edwards et al. |
| 7,922,699 B2 | 4/2011 | Baba et al. |
| 7,947,017 B2 | 5/2011 | Edwards et al. |
| 7,981,085 B2 | 7/2011 | Ethelfeld et al. |
| 7,988,675 B2 | 8/2011 | Gillespie, III |
| 7,993,301 B2 | 8/2011 | Boyd et al. |
| 7,998,117 B2 | 8/2011 | Gross et al. |
| 8,016,788 B2 | 9/2011 | Edwards et al. |
| 8,021,344 B2 | 9/2011 | Edwards et al. |
| 8,052,648 B2 | 11/2011 | Dikeman et al. |
| 8,088,096 B2 | 1/2012 | Lauchard et al. |
| 8,105,281 B2 | 1/2012 | Edwards et al. |
| 8,123,719 B2 | 2/2012 | Edwards et al. |
| 8,123,724 B2 | 2/2012 | Gillespie, III et al. |
| 8,162,898 B1 | 4/2012 | Wright |
| 8,172,082 B2 | 5/2012 | Edwards et al. |
| 8,172,804 B2 | 5/2012 | Bikovsky |
| 8,202,249 B2 | 6/2012 | Iio et al. |
| 8,206,351 B2 | 6/2012 | Sugimoto et al. |
| 8,206,360 B2 | 6/2012 | Edwards et al. |
| 8,226,610 B2 | 7/2012 | Edwards et al. |
| 8,226,615 B2 | 7/2012 | Bikovsky |
| 8,231,573 B2 | 7/2012 | Edwards et al. |
| 8,287,500 B2 | 10/2012 | Baba et al. |
| 8,298,171 B2 | 10/2012 | Ishikawa et al. |
| 8,303,535 B2 | 11/2012 | Both et al. |
| 8,303,549 B2 | 11/2012 | Mejlhede et al. |
| 8,313,466 B2 | 11/2012 | Edwards et al. |
| 8,348,898 B2 | 1/2013 | Cabiri |
| 8,361,026 B2 | 1/2013 | Edwards et al. |
| 8,361,027 B2 | 1/2013 | Gross et al. |
| 8,361,028 B2 | 1/2013 | Gross et al. |
| 8,361,029 B2 | 1/2013 | Edwards et al. |
| D676,549 S | 2/2013 | Lovell et al. |
| 8,409,141 B2 | 4/2013 | Johansen et al. |
| 8,425,462 B2 | 4/2013 | Edwards et al. |
| 8,433,383 B2 | 4/2013 | O'Neil et al. |
| 8,444,604 B2 | 5/2013 | Cindrich et al. |
| 8,475,414 B2 | 7/2013 | Boyd et al. |
| 8,512,287 B2 | 8/2013 | Cindrich et al. |
| 8,540,681 B2 | 9/2013 | Hetherington |
| 8,544,645 B2 | 10/2013 | Edwards et al. |
| 8,562,567 B2 | 10/2013 | Gundberg |
| 8,603,045 B2 | 12/2013 | Weber |
| 8,608,698 B2 | 12/2013 | Edwards et al. |
| 8,627,816 B2 | 1/2014 | Edwards et al. |
| 8,668,675 B2 | 3/2014 | Chase et al. |
| 8,679,055 B2 | 3/2014 | Ishikawa et al. |
| 8,679,395 B2 | 3/2014 | Nagel et al. |
| 8,690,827 B2 | 4/2014 | Edwards et al. |
| 8,690,836 B2 | 4/2014 | Mathews et al. |
| 8,708,971 B2 | 4/2014 | Segal |
| 8,740,847 B2 | 6/2014 | Levesque et al. |

(56) References Cited

U.S. PATENT DOCUMENTS

| | | |
|---|---|---|
| 8,771,239 B2 | 7/2014 | Boyd et al. |
| 8,808,244 B2 | 8/2014 | Adlon et al. |
| 8,834,419 B2 | 9/2014 | Jennings |
| 8,858,511 B2 | 10/2014 | Gonnelli et al. |
| 8,876,779 B2 | 11/2014 | Johansen et al. |
| 8,915,882 B2 | 12/2014 | Cabiri |
| 8,920,367 B2 | 12/2014 | Edwards et al. |
| 8,920,374 B2 | 12/2014 | Bokelman et al. |
| 8,920,377 B2 | 12/2014 | Edwards et al. |
| 8,926,594 B2 | 1/2015 | Edwards et al. |
| 8,939,935 B2 | 1/2015 | O'Connor et al. |
| 8,939,943 B2 | 1/2015 | Edwards et al. |
| D723,157 S | 2/2015 | Clemente et al. |
| 8,945,056 B2 | 2/2015 | Iio et al. |
| 8,956,331 B2 | 2/2015 | Johansen et al. |
| 8,961,469 B2 | 2/2015 | Sonderegger et al. |
| 8,974,413 B2 | 3/2015 | Baba et al. |
| 8,992,478 B2 | 3/2015 | Levesque |
| 9,022,022 B2 | 5/2015 | Edwards et al. |
| 9,056,170 B2 | 6/2015 | Edwards et al. |
| 9,072,839 B2 | 7/2015 | Kouyoumjian et al. |
| 9,078,976 B2 | 7/2015 | Boyd et al. |
| 9,084,849 B2 | 7/2015 | Edwards et al. |
| 9,101,706 B2 | 8/2015 | Gonnelli et al. |
| 9,107,996 B2 | 8/2015 | Brueggemann et al. |
| 9,132,231 B2 | 9/2015 | Gross |
| D741,995 S | 10/2015 | Prasser et al. |
| 9,149,575 B2 | 10/2015 | Cabiri |
| 9,149,578 B2 | 10/2015 | Byerly et al. |
| 9,149,579 B2 | 10/2015 | Edwards et al. |
| 9,149,582 B2 | 10/2015 | Sugimoto et al. |
| 9,155,844 B2 | 10/2015 | Brereton et al. |
| 9,173,999 B2 | 11/2015 | Edwards et al. |
| 9,180,244 B2 | 11/2015 | Anderson et al. |
| D745,142 S | 12/2015 | O'Connor et al. |
| 9,238,108 B2 | 1/2016 | Edwards et al. |
| 9,242,047 B2 | 1/2016 | Brereton et al. |
| 9,254,373 B2 | 2/2016 | Hoerdum et al. |
| 9,259,531 B2 | 2/2016 | Kamen et al. |
| 9,259,539 B2 | 2/2016 | Edwards et al. |
| 9,265,892 B2 | 2/2016 | Segal |
| 9,278,177 B2 | 3/2016 | Edwards et al. |
| 9,278,182 B2 | 3/2016 | Edwards et al. |
| 9,297,370 B2 | 3/2016 | Brueggemann et al. |
| 9,308,329 B2 | 4/2016 | Boyd et al. |
| 9,327,077 B2 | 5/2016 | Edwards et al. |
| 9,352,090 B2 | 5/2016 | Brereton et al. |
| 9,352,091 B2 | 5/2016 | Edwards et al. |
| 9,364,606 B2 | 6/2016 | Cindrich et al. |
| 9,364,612 B2 | 6/2016 | Hanson et al. |
| 9,375,532 B2 | 6/2016 | Brereton et al. |
| 9,408,984 B2 | 8/2016 | Durack et al. |
| 9,408,985 B2 | 8/2016 | Cronenberg et al. |
| D767,120 S | 9/2016 | Tyce et al. |
| D768,288 S | 10/2016 | O'Connor et al. |
| 9,463,280 B2 | 10/2016 | Cabiri et al. |
| 9,468,586 B2 | 10/2016 | Kvale et al. |
| 9,474,869 B2 | 10/2016 | Edwards et al. |
| 9,492,610 B2 | 11/2016 | Cabiri et al. |
| 9,492,618 B2 | 11/2016 | Day et al. |
| 9,504,793 B2 | 11/2016 | Eggert et al. |
| D774,640 S | 12/2016 | Tyce et al. |
| 9,511,189 B2 | 12/2016 | O'Connor et al. |
| 9,522,234 B2 | 12/2016 | Cabiri et al. |
| 9,526,837 B2 | 12/2016 | Carrel et al. |
| D776,262 S | 1/2017 | Tyce et al. |
| D776,263 S | 1/2017 | Tyce et al. |
| D776,264 S | 1/2017 | Tyce et al. |
| D776,265 S | 1/2017 | Tyce et al. |
| 9,533,092 B2 | 1/2017 | Gyrn et al. |
| 9,542,826 B2 | 1/2017 | Edwards et al. |
| 9,555,187 B2 | 1/2017 | Sonderegger et al. |
| 9,555,191 B2 | 1/2017 | Edwards et al. |
| 9,572,927 B2 | 2/2017 | Brueggemann et al. |
| 9,572,932 B2 | 2/2017 | Eggert et al. |
| 9,579,461 B2 | 2/2017 | Sonderegger et al. |
| 9,597,450 B2 | 3/2017 | Cindrich et al. |
| 9,604,003 B2 | 3/2017 | Brereton et al. |
| 9,610,407 B2 | 4/2017 | Bruggemann et al. |
| 9,623,181 B2 | 4/2017 | Brereton et al. |
| 9,636,451 B2 | 5/2017 | Gonnelli et al. |
| 9,636,459 B2 | 5/2017 | Brereton et al. |
| 9,656,021 B2 | 5/2017 | Brereton et al. |
| 9,675,752 B2 | 6/2017 | Christensen et al. |
| 9,687,607 B2 | 6/2017 | Brereton et al. |
| D791,306 S | 7/2017 | Clemente et al. |
| 2002/0123719 A1 | 9/2002 | Lavi et al. |
| 2002/0161332 A1 | 10/2002 | Ramey |
| 2003/0105430 A1 | 6/2003 | Lavi et al. |
| 2004/0015134 A1 | 1/2004 | Lavi et al. |
| 2004/0020558 A1 | 2/2004 | Stewart et al. |
| 2004/0030285 A1 | 2/2004 | Lavi et al. |
| 2004/0069044 A1 | 4/2004 | Lavi et al. |
| 2004/0092873 A1 | 5/2004 | Moberg |
| 2005/0065472 A1 | 3/2005 | Cindrich et al. |
| 2005/0197650 A1 | 9/2005 | Sugimoto et al. |
| 2007/0112326 A1 | 5/2007 | Bosshard et al. |
| 2007/0135767 A1 | 6/2007 | Gillespie, III |
| 2009/0048563 A1 | 2/2009 | Ethelfeld et al. |
| 2009/0093793 A1 | 4/2009 | Gross et al. |
| 2009/0143741 A1 | 6/2009 | Burn |
| 2010/0049128 A1 | 2/2010 | McKenzie et al. |
| 2011/0105872 A1 | 5/2011 | Chickering, III et al. |
| 2011/0137255 A1 | 6/2011 | Nielsen et al. |
| 2011/0137257 A1 | 6/2011 | Gyrn et al. |
| 2011/0152779 A1 | 6/2011 | Panotopoulos |
| 2011/0270220 A1 | 11/2011 | Genosar |
| 2012/0022499 A1 | 1/2012 | Anderson et al. |
| 2012/0035546 A1 | 2/2012 | Cabiri |
| 2012/0071837 A1 | 3/2012 | O'Connor et al. |
| 2012/0123387 A1 | 5/2012 | Gonzalez et al. |
| 2012/0130318 A1 | 5/2012 | Young |
| 2012/0238962 A1 | 9/2012 | Chin et al. |
| 2012/0253314 A1 | 10/2012 | Harish et al. |
| 2012/0310173 A1 | 12/2012 | Sonderegger et al. |
| 2012/0310175 A1 | 12/2012 | Vedrine et al. |
| 2012/0323183 A1 | 12/2012 | Peterson et al. |
| 2012/0330235 A1 | 12/2012 | Moga et al. |
| 2013/0006195 A1 | 1/2013 | Sonderegger et al. |
| 2013/0012872 A1 | 1/2013 | Gross et al. |
| 2013/0012874 A1 | 1/2013 | Gross et al. |
| 2013/0012875 A1 | 1/2013 | Gross et al. |
| 2013/0066274 A1 | 3/2013 | O'Connor et al. |
| 2013/0079747 A1 | 3/2013 | Gross et al. |
| 2013/0090605 A1 | 4/2013 | O'Connor et al. |
| 2013/0211374 A1 | 8/2013 | Hetherington |
| 2013/0218089 A1 | 8/2013 | Davies et al. |
| 2013/0218092 A1 | 8/2013 | Davies et al. |
| 2013/0237916 A1 | 9/2013 | Hanson et al. |
| 2013/0281932 A1 | 10/2013 | Harish et al. |
| 2013/0310757 A1 | 11/2013 | Brereton et al. |
| 2013/0317427 A1 | 11/2013 | Brereton et al. |
| 2013/0317430 A1 | 11/2013 | Brereton et al. |
| 2014/0005596 A1 | 1/2014 | Schuster |
| 2014/0008366 A1 | 1/2014 | Genosar |
| 2014/0083517 A1 | 3/2014 | Moia et al. |
| 2014/0088553 A1 | 3/2014 | Hetherington |
| 2014/0128815 A1 | 5/2014 | Cabiri et al. |
| 2014/0148760 A1 | 5/2014 | Ishikawa et al. |
| 2014/0148784 A1 | 5/2014 | Anderson et al. |
| 2014/0171871 A1 | 6/2014 | Mathews et al. |
| 2014/0171872 A1 | 6/2014 | Mathews et al. |
| 2014/0200510 A1 | 7/2014 | Agard et al. |
| 2014/0213975 A1 | 7/2014 | Clemente et al. |
| 2014/0236086 A1 | 8/2014 | Levesque et al. |
| 2014/0236096 A1 | 8/2014 | Helmer et al. |
| 2014/0238542 A1 | 8/2014 | Kvale |
| 2014/0243749 A1 | 8/2014 | Edwards et al. |
| 2014/0288511 A1 | 9/2014 | Tan-Malecki et al. |
| 2014/0296787 A1 | 10/2014 | Agard et al. |
| 2014/0296824 A1 | 10/2014 | Edwards et al. |
| 2014/0316376 A1 | 10/2014 | Wall |
| 2014/0336578 A1 | 11/2014 | Brereton et al. |
| 2015/0011973 A1 | 1/2015 | Edwards et al. |

(56) References Cited

U.S. PATENT DOCUMENTS

| | | |
|---|---|---|
| 2015/0057613 A1 | 2/2015 | Clemente et al. |
| 2015/0080800 A1 | 3/2015 | Cronenberg |
| 2015/0088077 A1 | 3/2015 | Kemp et al. |
| 2015/0126926 A1 | 5/2015 | Giambattista et al. |
| 2015/0157786 A1 | 6/2015 | Sonderegger et al. |
| 2015/0157804 A1 | 6/2015 | Baba et al. |
| 2015/0174323 A1 | 6/2015 | Edwards et al. |
| 2015/0174326 A1 | 6/2015 | Bokelman et al. |
| 2015/0190588 A1 | 7/2015 | Hanson et al. |
| 2015/0202367 A1 | 7/2015 | Plaschkes et al. |
| 2015/0209505 A1 | 7/2015 | Hanson et al. |
| 2015/0209519 A1 | 7/2015 | Mernøe |
| 2015/0217045 A1 | 8/2015 | Bente et al. |
| 2015/0231336 A1 | 8/2015 | Edwards et al. |
| 2015/0290392 A1 | 10/2015 | Henderson et al. |
| 2015/0297827 A1 | 10/2015 | Hanson et al. |
| 2015/0306306 A1 | 10/2015 | Gonnelli et al. |
| 2015/0306307 A1 | 10/2015 | Cole et al. |
| 2015/0359965 A1 | 12/2015 | O'Connor et al. |
| 2015/0374912 A1 | 12/2015 | Sugimoto et al. |
| 2016/0008542 A1 | 1/2016 | Hirschel et al. |
| 2016/0015907 A1 | 1/2016 | Edwards et al. |
| 2016/0022909 A1 | 1/2016 | Edwards et al. |
| 2016/0030665 A1 | 2/2016 | Cabiri |
| 2016/0045670 A1 | 2/2016 | Edwards et al. |
| 2016/0045673 A1 | 2/2016 | Bayer et al. |
| 2016/0058541 A1 | 3/2016 | Wu et al. |
| 2016/0058945 A1 | 3/2016 | Piscitelli |
| 2016/0058949 A1 | 3/2016 | Bayer et al. |
| 2016/0067417 A1 | 3/2016 | Bayer et al. |
| 2016/0082182 A1 | 3/2016 | Gregory et al. |
| 2016/0082189 A1 | 3/2016 | Anderson et al. |
| 2016/0089056 A1 | 3/2016 | Limaye et al. |
| 2016/0106912 A1 | 4/2016 | Gross et al. |
| 2016/0106923 A1 | 4/2016 | Brereton et al. |
| 2016/0121056 A1 | 5/2016 | Edwards et al. |
| 2016/0129194 A1 | 5/2016 | Brereton et al. |
| 2016/0129202 A1 | 5/2016 | Carrel et al. |
| 2016/0158435 A1 | 6/2016 | Wu et al. |
| 2016/0158463 A1 | 6/2016 | Kamen et al. |
| 2016/0175515 A1 | 6/2016 | McCullough |
| 2016/0175527 A1 | 6/2016 | McCullough |
| 2016/0184514 A1 | 6/2016 | Kamen et al. |
| 2016/0184521 A1 | 6/2016 | Edwards et al. |
| 2016/0184535 A1 | 6/2016 | Edwards et al. |
| 2016/0193405 A1 | 7/2016 | Schabbach et al. |
| 2016/0213838 A1 | 7/2016 | Schabbach et al. |
| 2016/0213840 A1 | 7/2016 | Schabbach et al. |
| 2016/0228644 A1 | 8/2016 | Cabiri et al. |
| 2016/0235916 A1 | 8/2016 | Edwards et al. |
| 2016/0243318 A1 | 8/2016 | Despa et al. |
| 2016/0250414 A1 | 9/2016 | Edwards et al. |
| 2016/0262984 A1 | 9/2016 | Arnott et al. |
| 2016/0271323 A1 | 9/2016 | Brüggemann et al. |
| 2016/0279330 A1 | 9/2016 | Schabbach et al. |
| 2016/0317736 A1 | 11/2016 | Schabbach et al. |
| 2016/0325044 A1 | 11/2016 | Tschirren et al. |
| 2016/0354553 A1 | 12/2016 | Anderson et al. |
| 2016/0367752 A1 | 12/2016 | Cindrich et al. |
| 2017/0021096 A1 | 1/2017 | Cole et al. |
| 2017/0021103 A1 | 1/2017 | Mosebach et al. |
| 2017/0021137 A1 | 1/2017 | Cole |
| 2017/0028132 A1 | 2/2017 | Cronenberg et al. |
| 2017/0035957 A1 | 2/2017 | Edwards et al. |
| 2017/0035961 A1 | 2/2017 | Cabiri |
| 2017/0043101 A1 | 2/2017 | Cole et al. |
| 2017/0049954 A1 | 2/2017 | Edwards et al. |
| 2017/0049958 A1 | 2/2017 | Cronenberg et al. |
| 2017/0049965 A1 | 2/2017 | Baker et al. |
| 2017/0080149 A1 | 3/2017 | O'Connor et al. |
| 2017/0092101 A1 | 3/2017 | Edwards et al. |
| 2017/0095614 A1 | 4/2017 | Sonderegger et al. |
| 2017/0098058 A1 | 4/2017 | McCullough et al. |
| 2017/0103186 A1 | 4/2017 | McCullough et al. |
| 2017/0119959 A1 | 5/2017 | Cole et al. |
| 2017/0119969 A1 | 5/2017 | McCullough et al. |
| 2017/0124284 A1 | 5/2017 | McCullough et al. |
| 2017/0124285 A1 | 5/2017 | McCullough et al. |
| 2017/0128665 A1 | 5/2017 | Mathews et al. |
| 2017/0143908 A1 | 5/2017 | Eggert et al. |
| 2017/0165418 A1 | 6/2017 | Bainton et al. |
| 2017/0182242 A1 | 6/2017 | Galitz et al. |
| 2017/0182243 A1 | 6/2017 | Cole et al. |
| 2017/0189609 A1 | 7/2017 | Wei |
| 2017/0189610 A1 | 7/2017 | Gonnelli et al. |

FOREIGN PATENT DOCUMENTS

| | | |
|---|---|---|
| EP | 1646412 B1 | 3/2007 |
| EP | 1465689 B1 | 9/2009 |
| EP | 1855754 B1 | 9/2009 |
| EP | 1696981 B1 | 10/2009 |
| EP | 2219710 B1 | 4/2011 |
| EP | 2301611 B1 | 8/2012 |
| EP | 2608825 B1 | 8/2014 |
| EP | 2571549 B1 | 2/2016 |
| EP | 2300078 B1 | 3/2016 |
| EP | 3000497 A3 | 7/2016 |
| EP | 2736565 B1 | 7/2017 |
| GB | 2467904 A | 8/2010 |
| WO | 03024511 A1 | 3/2003 |
| WO | 2004075955 A1 | 9/2004 |
| WO | 2008091838 A2 | 7/2008 |
| WO | 2010029054 A1 | 3/2010 |
| WO | 2010035057 A1 | 4/2010 |
| WO | 2010035059 A1 | 4/2010 |
| WO | 2011014514 A1 | 2/2011 |
| WO | 2011060197 A1 | 5/2011 |
| WO | 2011084951 A2 | 7/2011 |
| WO | 2011133823 A1 | 10/2011 |
| WO | 2012032411 A2 | 3/2012 |
| WO | 2013155153 A1 | 10/2013 |
| WO | 2014037946 A1 | 3/2014 |
| WO | 2014106096 A1 | 7/2014 |
| WO | 2014/149357 A1 | 9/2014 |
| WO | 2015024960 A1 | 2/2015 |
| WO | 2015081337 A2 | 6/2015 |
| WO | 2015123688 A1 | 8/2015 |
| WO | 2015185176 A1 | 12/2015 |
| WO | 2016041871 A1 | 3/2016 |
| WO | 2016041873 A1 | 3/2016 |
| WO | 2016049532 A1 | 3/2016 |
| WO | 2016053954 A1 | 4/2016 |
| WO | 2016074850 A1 | 5/2016 |
| WO | 2016100781 A1 | 6/2016 |
| WO | 2016115372 A1 | 7/2016 |
| WO | 2016130679 A2 | 8/2016 |
| WO | 2016141082 A1 | 9/2016 |
| WO | 2016210404 A1 | 12/2016 |
| WO | 2017050781 A1 | 3/2017 |
| WO | 2017089271 A1 | 6/2017 |
| WO | 2017089287 A1 | 6/2017 |
| WO | 2017089288 A1 | 6/2017 |
| WO | 2017141255 A1 | 8/2017 |

OTHER PUBLICATIONS

Verjans et al. "A New Concept in Aseptic Filling: Closed-Vial Technology", Pharmaceutical Technology, 4 pages, May 2005.
European Examination Report dated Aug. 10, 2018 in European Application No. 16713195.2 (8 pages).

* cited by examiner

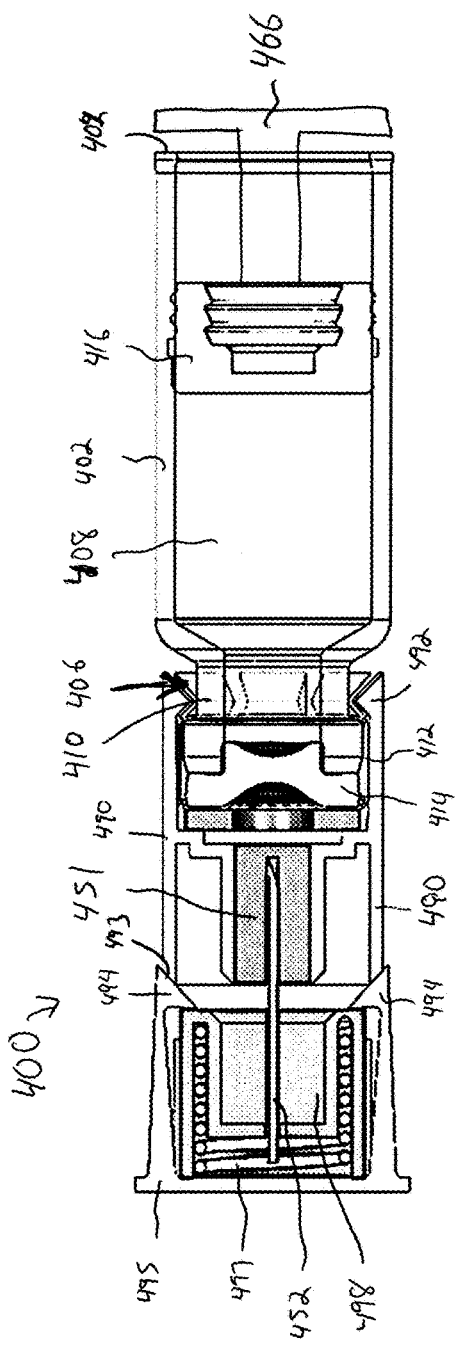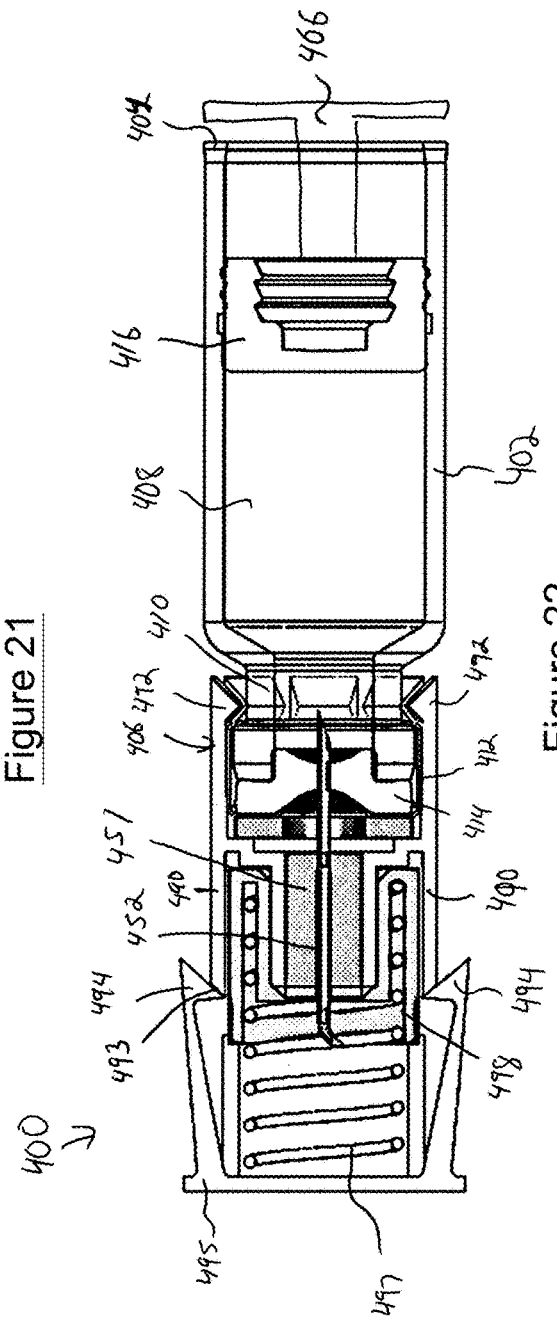
Figure 21
Figure 22

ASEPTIC PIERCING SYSTEM AND METHOD

CROSS REFERENCE TO RELATED APPLICATION

This application claims priority benefit under 35 U.S.C. § 119(e) to U.S. Provisional Application No. 62/130,718, filed Mar. 10, 2015, and entitled Aseptic Piercing System and Method, the entirety of which is incorporated herein by reference in its entirety.

FIELD OF THE INVENTION

The present invention relates generally to delivery systems for administering medication. More specifically, but not exclusively, the present invention concerns aseptic piercing systems.

BACKGROUND OF THE INVENTION

Currently before a needle is introduced into a vial, primary container or cartridge, it is necessary to use an alcohol wipe to sterilize the face of the vial septum in order to maintain a sterile environment. If sterilization of the vial septum is not properly performed, the medication may be contaminated or contaminants may be delivered to the patient. Further, such wiping is an extra step to perform and it is not practical if the container is inside a delivery device. Typically, wiping the face of the vial septum also adds another step in the sterilization process.

Thus, an aseptic piercing system that ensures a sterile environment without the risk of contamination is desirable.

SUMMARY OF THE INVENTION

Aspects of the present disclosure provide aseptic vial piercing and sterilization systems. The present disclosure also provides methods for assembling, using and sterilizing the aseptic vial piercing systems.

In one aspect, the present disclosure provides a method of forming an aseptic primary container piercing mechanism. The method includes obtaining a pre-sterilized primary container including a first end, a first cavity, a second end with an opening in communication with the first cavity, a septum at least partially sealing the opening, and a product within the first cavity. The method further includes obtaining an injection assembly including a first end portion of a hollow flowpath forming member. The method also includes assembling the injection assembly with the second end of the primary container in a non-sterile environment to form a second cavity extending about the first end portion of the flowpath forming member and to the primary container. Further, the method includes terminally sterilizing the second cavity and the first end portion of the flowpath forming member therein.

In some embodiments, the prior to the terminally sterilizing, the second cavity and the first end portion of the flowpath forming member may be non-sterile. In some embodiments, terminally sterilizing the second cavity and the first end portion of the flowpath forming member may include injecting a sterilient through the flowpath forming member and thereby into the second cavity. In some such embodiments, the sterilient may be introduced into the flowpath forming member via a second end portion of the flowpath forming member positioned exterior to the injection assembly.

In some other such embodiments, the primary container may include a boot portion that forms the second cavity. In some such embodiments, the boot portion and the septum may be integral. In some other such embodiments, assembling the injection assembly with the second end of the primary container may insert the flowpath forming member through an opening of the boot portion that forms a sliding seal about the flowpath forming member extending therethrough. In some such embodiments, the opening may be configured to vent positive pressure such that the injected sterilient flushes out the atmosphere within the flowpath forming member and the second cavity. In some such embodiments, the method may further include injecting an inert gas through the flowpath forming member and, thereby into the second cavity to flush out the sterilient from the flowpath forming member and the second cavity.

In some embodiments, the assembly of the injection assembly and the primary container may be configured such that axial translation of the primary container toward the first end portion of the flowpath forming member effectuates the flowpath forming member being driven through the boot member and the septum such that the flowpath forming member extends through the second cavity and the first end portion is positioned within the first cavity in fluid communication with the product. In some such embodiments, the primary container may be axially translated with respect to the first end portion of the flowpath forming member for a distance to impale the boot member and the septum on the first end portion of the flowpath forming member such that the flowpath forming member extends through the second cavity and the first end portion is positioned within the first cavity in fluid communication with the product. In some other such embodiments, the primary container may be axially translated with respect to the first end portion of the flowpath forming member to such an extent that actuation of the injection assembly is triggered and the injection assembly thereby axially drives the flowpath forming member toward the primary container to impale the first end portion of the flowpath forming member through the boot member and the septum such that the flowpath forming member extends through the second cavity and the first end portion is positioned within the first cavity in fluid communication with the product. In some such embodiments, the actuation of the injection assembly may release preloaded energy of a resilient member of the injection assembly to axially drive a driver member coupled to the flowpath forming member.

In some embodiments, the first end portion of the flowpath forming member may be sterile and capped with a capping member, and the injection assembly may include a permeable window in communication with the second cavity. In some such embodiments, terminally sterilizing the second cavity and the first end portion of the flowpath forming member may include at least one: diffusing a sterilient through the permeable window and into the second cavity and thereby into the first end portion; and directing ultraviolet light through the permeable window and into the second cavity.

In another aspect, the present disclosure provides an aseptic piercing system including a sterile primary container and an injection assembly including a flowpath forming member assembled with the primary container. The sterile primary container includes a first end, a first cavity, a second end with an opening in communication with the first cavity, a septum at least partially sealing the opening, a product within the first cavity, and a boot portion that forms a second cavity. The flowpath member extends through an opening of the boot portion such that a first end portion of the flowpath forming member is positioned within the second cavity. The opening of the boot portion forms a sliding seal about the flowpath forming member. Axial translation of the primary container toward the first end portion of the flowpath forming member effectuates relative translation of the first end portion of the flowpath forming member and the boot member and the septum of the primary container such that the flowpath forming member extends through the second cavity and the first end portion is positioned within the first cavity in fluid communication with the product.

In some embodiments, the boot portion and the septum may be integral, and the sliding seal may be configured to vent positive pressure within the second cavity. In some embodiments, axial translation of the primary container with respect to the first end portion of the flowpath forming member may impale the boot member and the septum over the first end portion of the flowpath forming member such that the flowpath forming member extends through the second cavity and the first end portion is positioned within the first cavity in fluid communication with the product.

In some embodiments, a second end portion of the flowpath forming member may be positioned exterior to the injection assembly within a sealed third cavity. In some embodiments, the axial translation of the primary container with respect to the first end portion of the flowpath forming member may actuate the injection assembly to axially drive the flowpath forming member toward the primary container to impale the first end portion of the flowpath forming member through the boot member and the septum such that the flowpath forming member extends through the second cavity and the first end portion is positioned within the first cavity in fluid communication with the product. In some such embodiments, the injection assembly may include a collar fixed to the second end of the primary container, a driver retainer axially slidably coupled to the collar, a driver member axially slidably coupled to the driver retainer and fixed to the flowpath forming member, and a resilient member positioned between a portion of the driver retainer and the driver member. In some such embodiments, in a pre-actuated state of the system, the resilient member may exert a preload force on the driver member acting axially toward the second end of the primary container, and wherein actuation of the injection system releases the preload force of the resilient member on the driver member to axially drive the flowpath forming member toward the primary container to impale the first end portion of the flowpath forming member through the boot member and the septum such that the flowpath forming member extends through the second cavity and the first end portion is positioned within the first cavity in fluid communication with the product.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the present disclosure and together with the detailed description herein, serve to explain the principles of the present disclosure. The drawings are only for purposes of illustrating preferred embodiments and are not to be construed as limiting the present disclosure. It is emphasized that, in accordance with the standard practice in the industry, various features are not drawn to scale. In fact, the dimensions of the various features may be arbitrarily increased or reduced for clarity of discussion. The foregoing and other objects, features and advantages of the present disclosure are apparent from the following detailed description taken in conjunction with the accompanying drawings in which:

FIG. 21 is an assembled cross-sectional view of an aseptic vial piercing system in a pre-activated state, in accordance with another aspect of the present invention;

FIG. 22 is an assembled cross-sectional view of the aseptic vial piercing system of FIG. 21 in an activated state with a flowpath forming member aseptically coupled in fluid communication with a primary container, in accordance with another aspect of the present invention.

DETAILED DESCRIPTION FOR CARRYING OUT THE INVENTION

Figure 1:
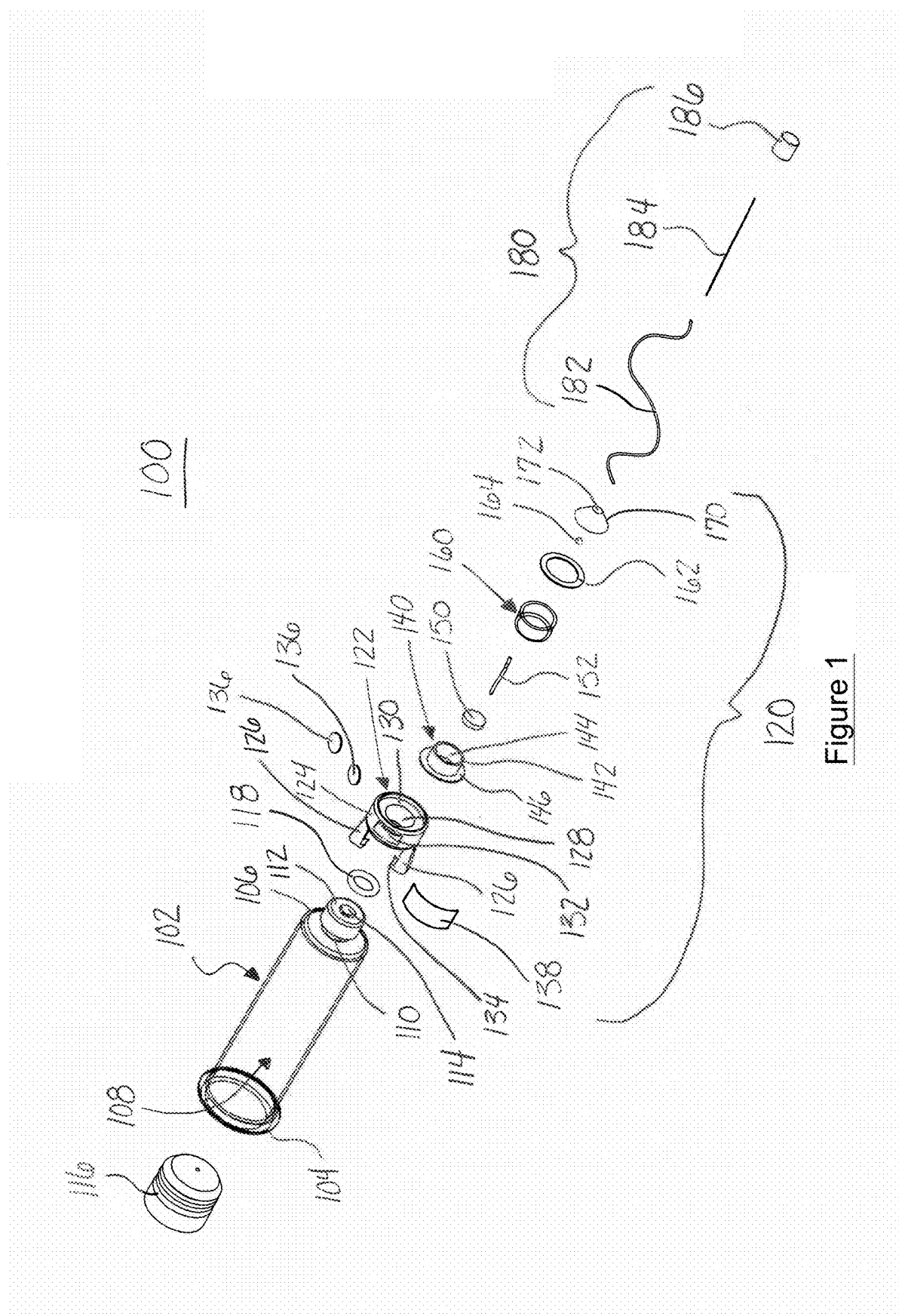
FIG. 1 is an exploded, perspective view of an aseptic vial piercing system, in accordance with an aspect of the present invention.

Generally stated, disclosed herein is are aseptic vial piercing and sterilization systems. Further, methods of assembling, using and sterilizing the aseptic vial, primary container and/or cartridge piercing systems are discussed. The systems and methods provide for piercing of a vial, primary container or cartridge with a flow-path mechanism (e.g., a needle) under sterile conditions, without having to perform an alcohol wipe and/or to assemble the drug container into the device or similar patient/provider interaction to sterilize the piercing site.

In this detailed description and the following claims, the words proximal, distal, anterior, posterior, medial, lateral, superior and inferior are defined by their standard usage for indicating a particular part of a device according to the relative disposition of the device with respect to a body or directional terms of reference. For example, "proximal" means the portion of a device nearest the point of attachment, while "distal" indicates the portion of the device farthest from the point of attachment. As for directional terms, "anterior" is a direction towards the front side of the device, "posterior" means a direction towards the back side of the device, "medial" means towards the midline of the device, "lateral" is a direction towards the sides or away from the midline of the device, "superior" means a direction above and "inferior" means a direction below another object or structure.

Referring to the drawings, wherein like reference numerals are used to indicate like or analogous components throughout the several views, and with particular reference to FIGS. 1-14, there is illustrated an aseptic piercing system 100. The terms "aseptic piercing system," "aseptic vial piercing system," and "aseptic cartridge piercing system" may be used interchangeably herein as they essentially refer to an aseptic flowpath-forming mechanism (e.g., a needle) piercing system or structure. The aseptic piercing system 100 includes a primary container, chamber, syringe, vial, or cartridge 102 with a first end 104 and a second end 106. The primary container or vial 102 may also include a cavity 108 opened at the first end 104 and extending toward the second end 106. The second end 106 may include a neck 110 with a cap 112 engaging the neck 110 to close the second end 106 of the primary container or vial 102. A septum 114 may be positioned between the primary container or vial 102 and the cap 112 to assist with closing the second end 106 of the primary container or vial 102 and allow for a needle 152 (e.g., a staked needle) to be inserted into the primary container or vial 102 via through the septum. The cavity 108 of the primary container or vial 102 may be sized to receive a piston 116 to close the first end 104 of the primary container or vial 102 when a medication or fluid is inside of the cavity 108. The piston 116 may also assist with delivery of the medication or fluid, as explained further below. The aseptic piercing system 100 may also include a seal 118. The seal 118 may be, for example, ring shaped and sized to engage the cap 112 and surround the septum 114.

Figure 2:
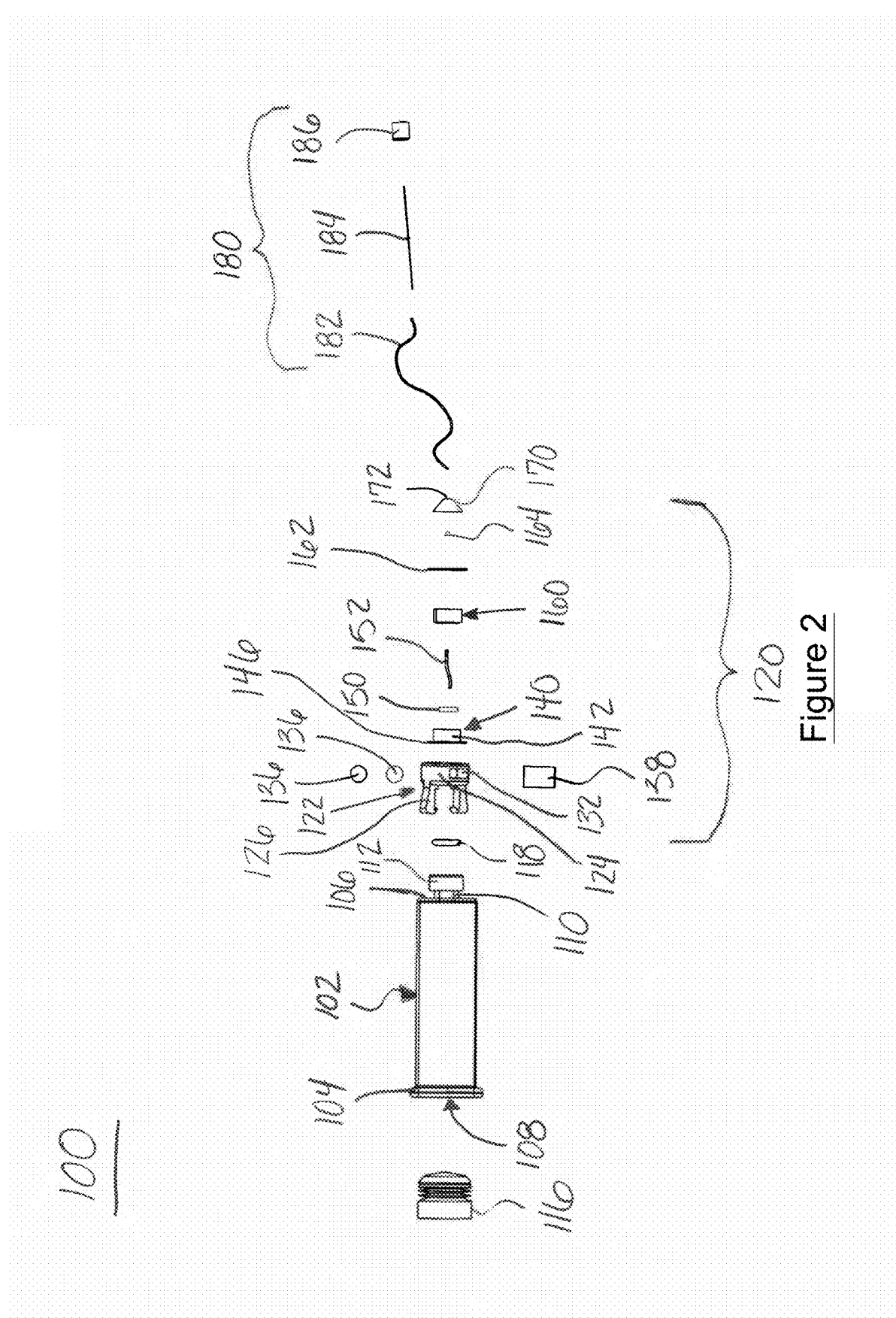
FIG. 2 is an exploded, side view of the aseptic vial piercing system of FIG. 1, in accordance with an aspect of the present invention.
Figure 3:
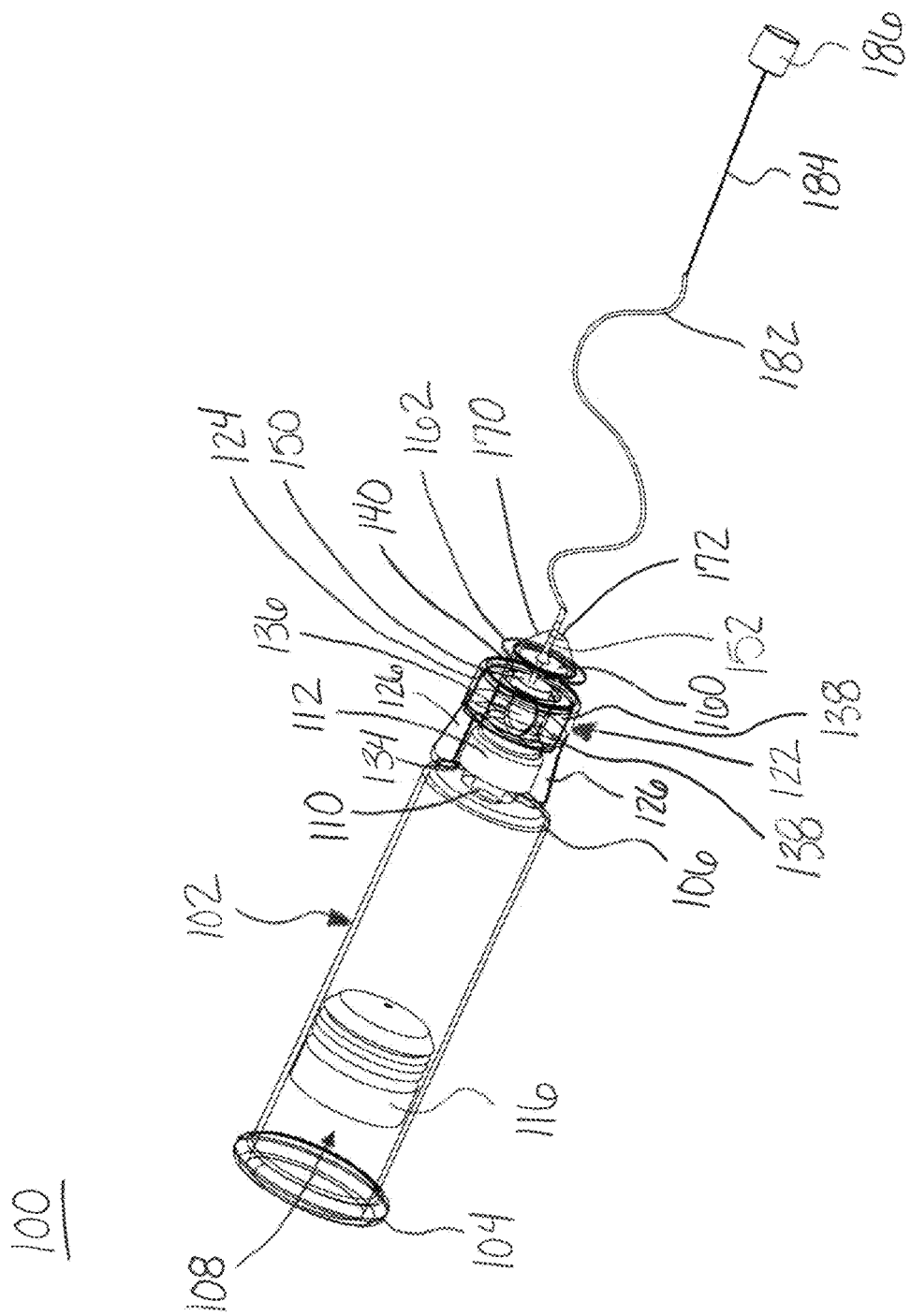
FIG. 3 is an assembled, perspective view of the aseptic vial piercing system of FIG. 1 with a transparent connector assembly, in accordance with an aspect of the present invention.
Figure 4:
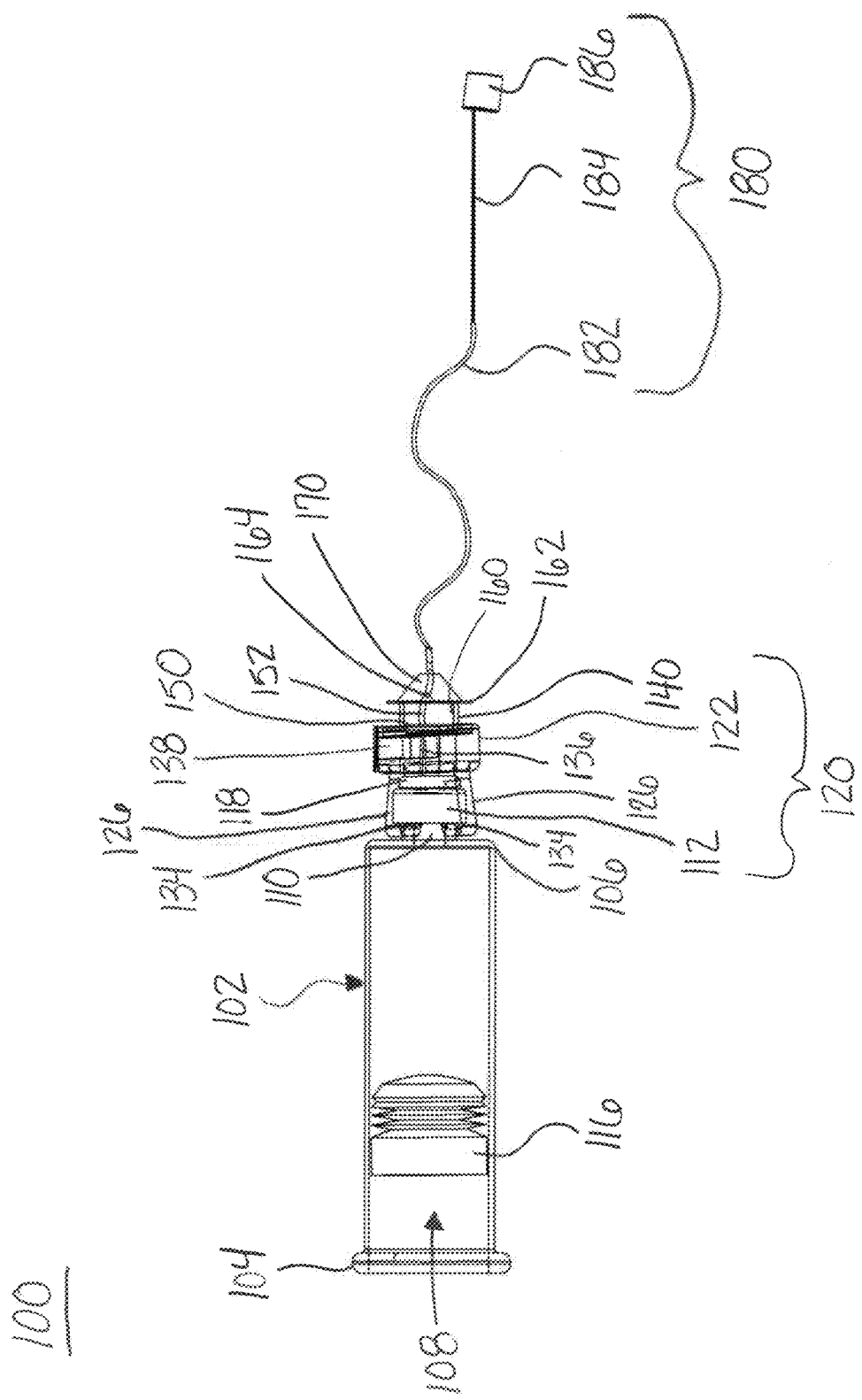
FIG. 4 is a side view of the aseptic vial piercing system of FIG. 3 with a transparent connector assembly, in accordance with an aspect of the present invention.
Figure 5:
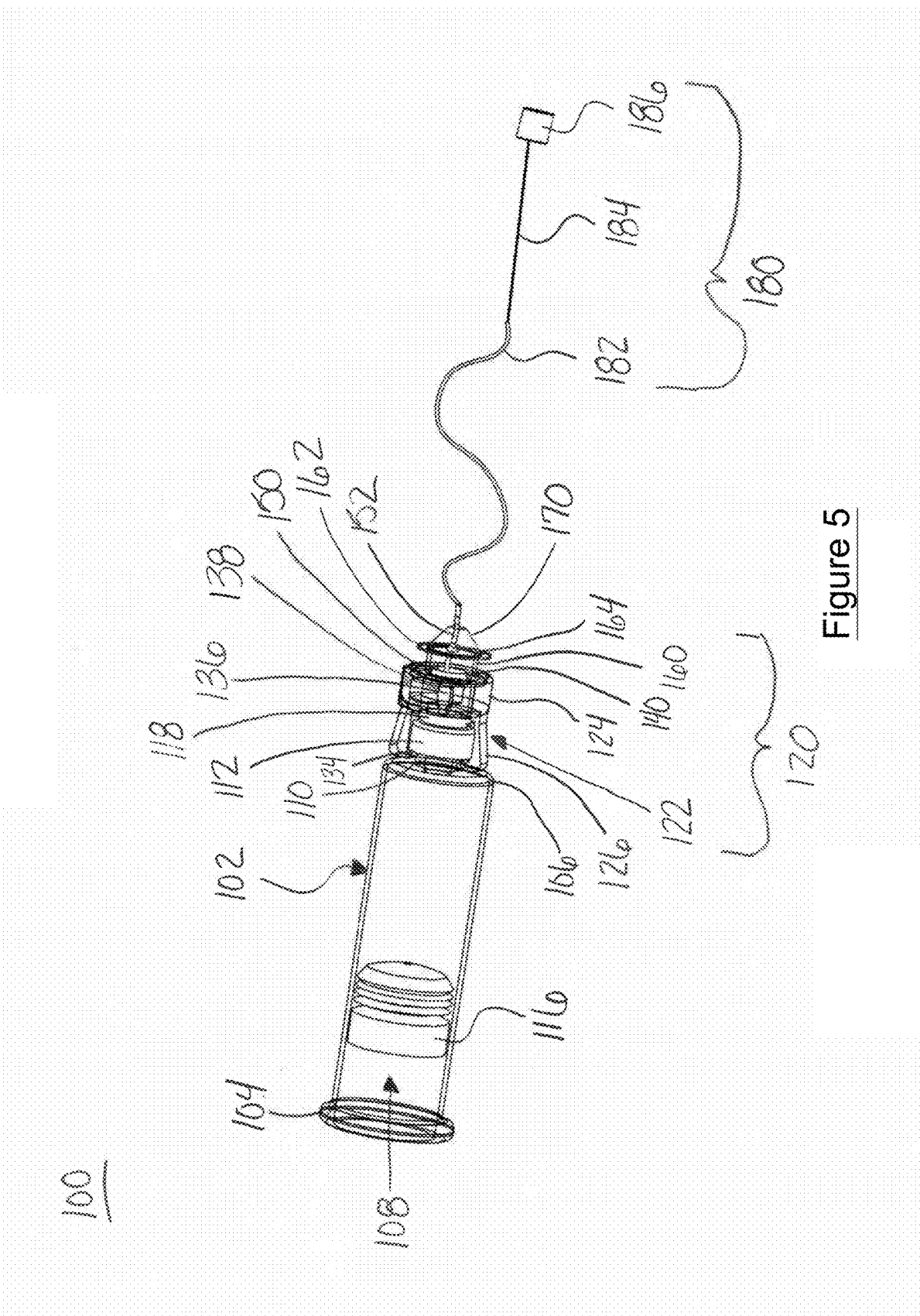
FIG. 5 is a perspective view of the assembled aseptic vial piercing system of FIG. 3 with a transparent connector assembly, in accordance with an aspect of the present invention.
Figure 6:
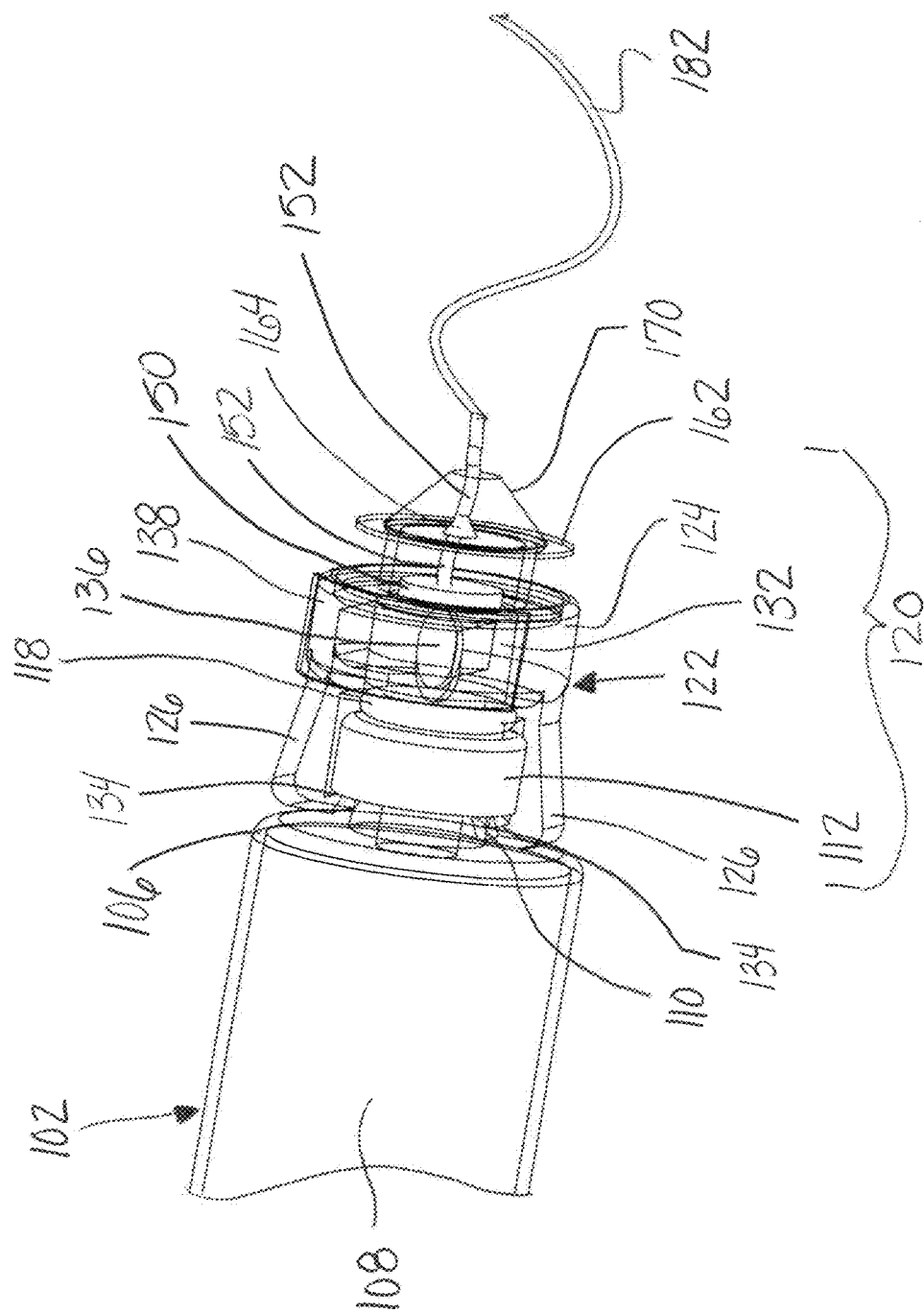
FIG. 6 is an enlarged perspective view of a portion of the aseptic vial piercing system of FIG. 3, in accordance with an aspect of the present invention.
Figure 7:
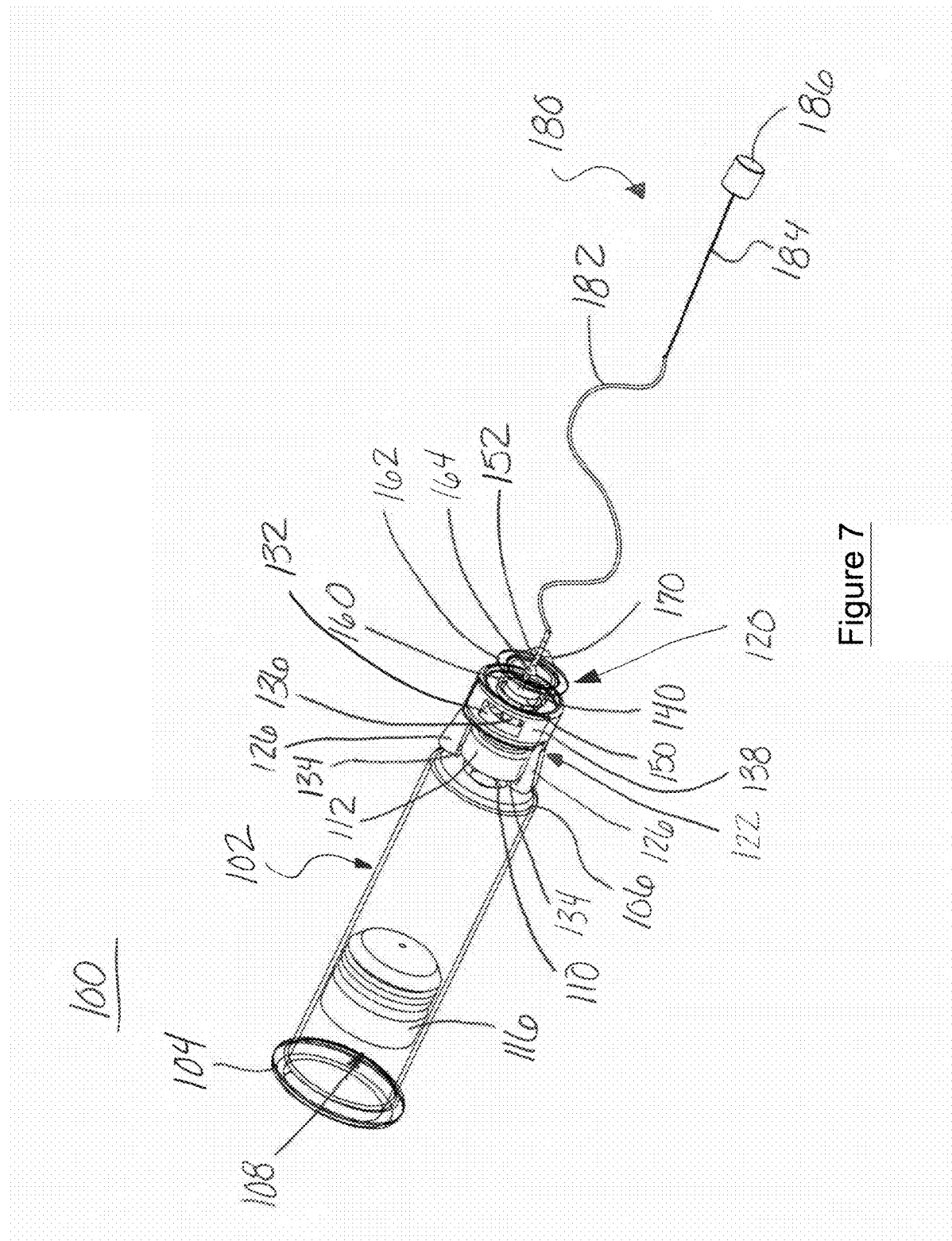
FIG. 7 is an assembled, perspective view of the aseptic vial piercing system of FIG. 1 with a transparent window seal, support member, collapsible member, support ring, and impact cushion, in accordance with an aspect of the present invention.
Figure 8:
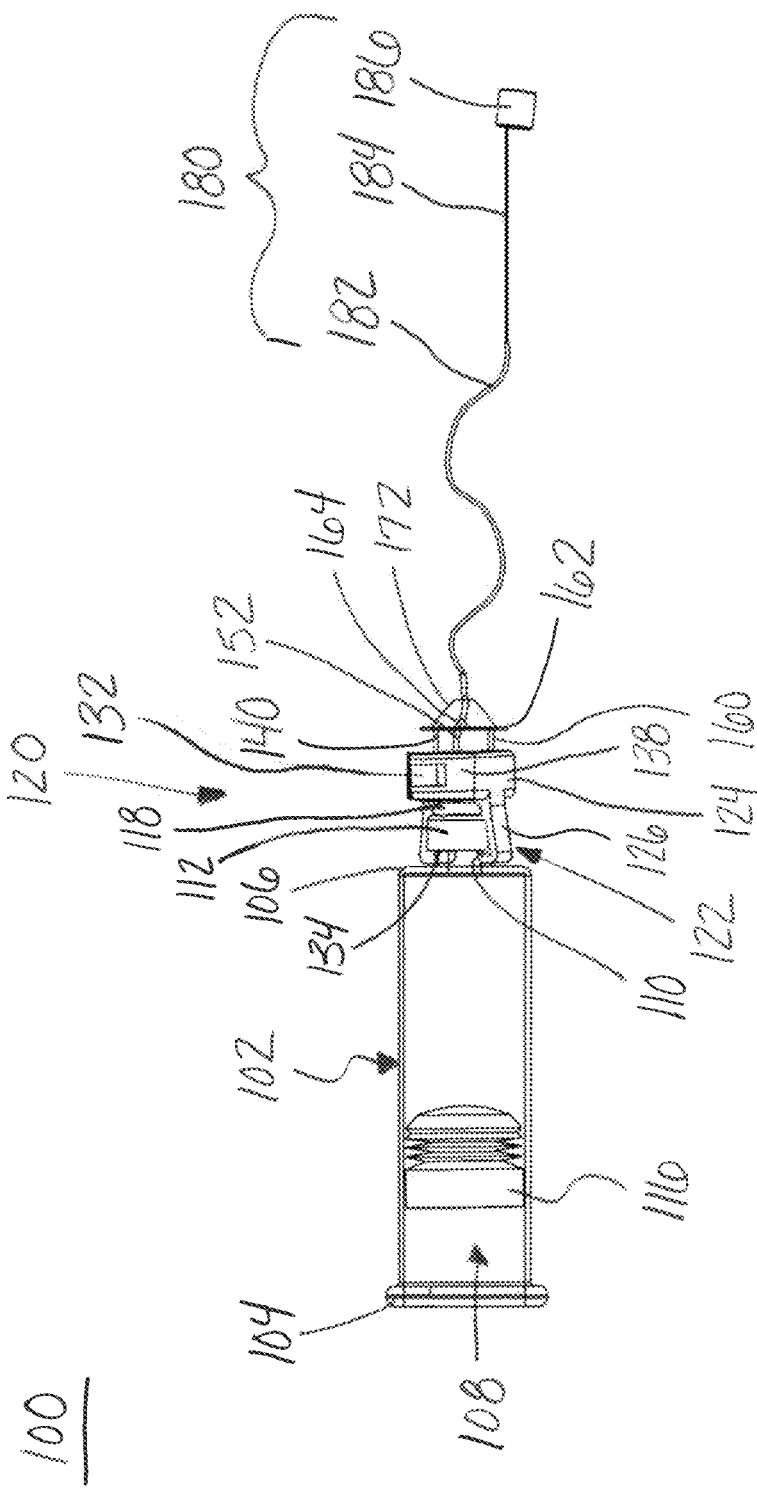
FIG. 8 is a side view of the aseptic vial piercing system of FIG. 7, in accordance with an aspect of the present invention.
Figure 9:
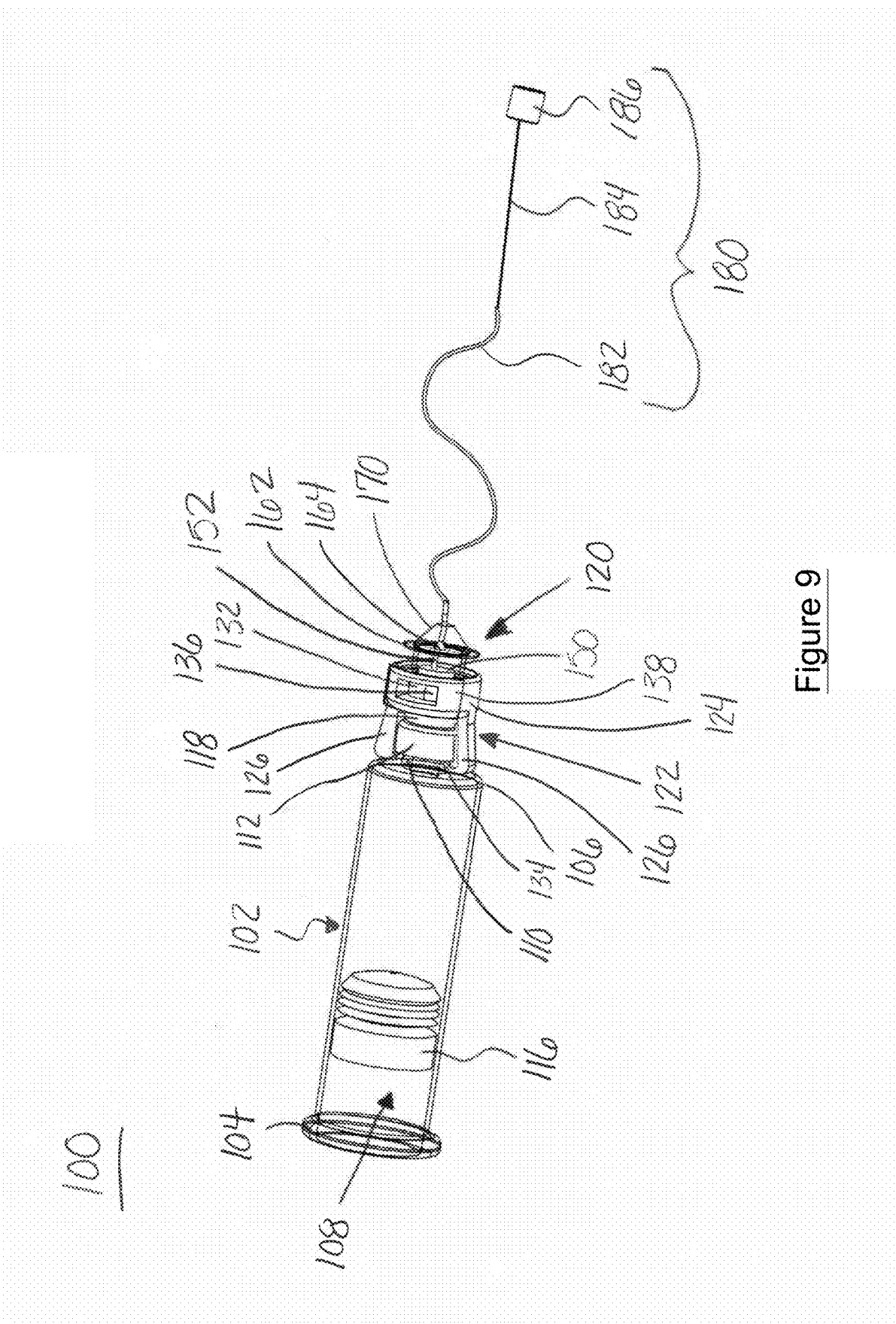
FIG. 9 is a perspective view of the aseptic vial piercing system of FIG. 7, in accordance with an aspect of the present invention.
Figure 10:
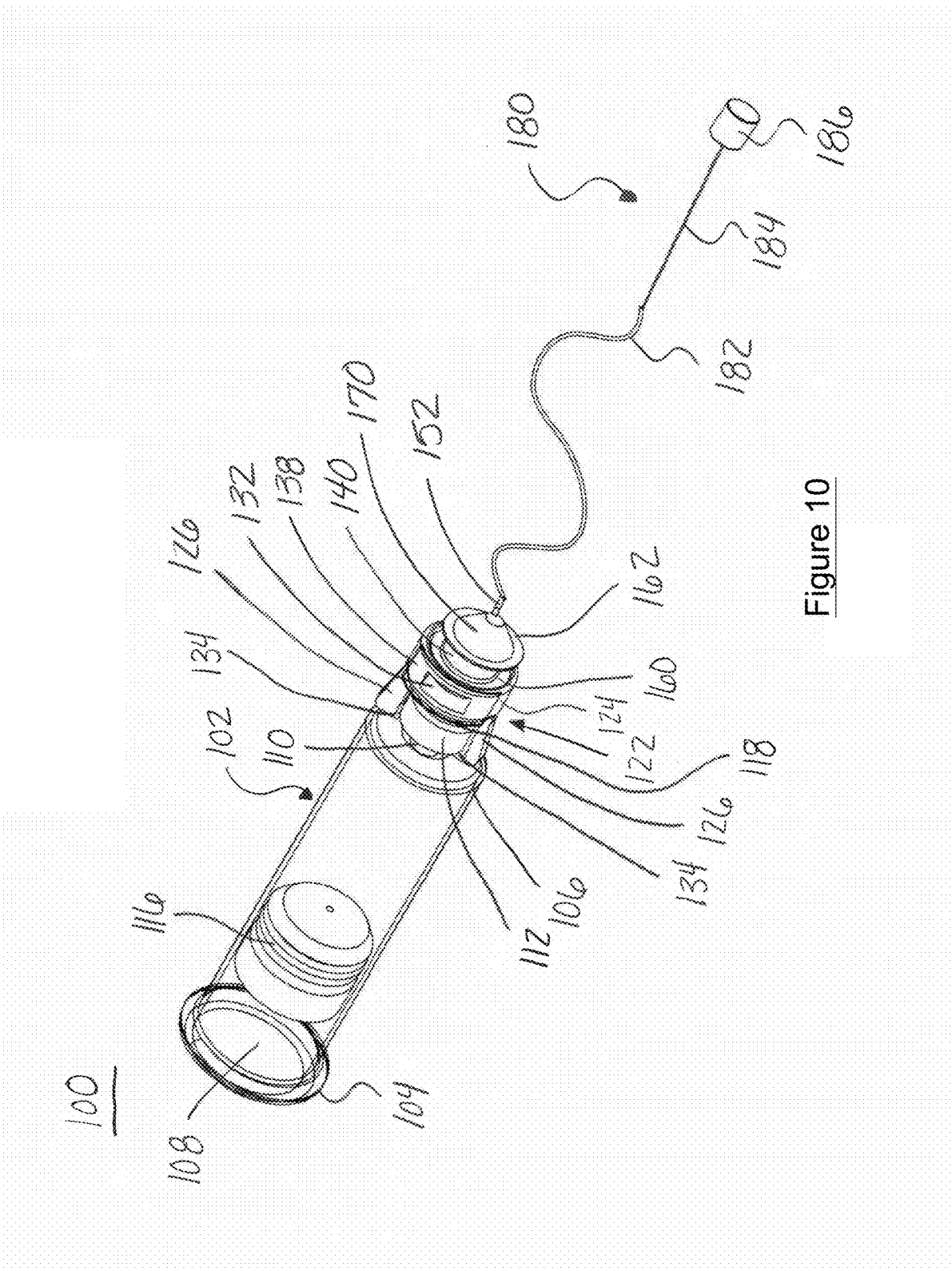
FIG. 10 is an assembled, perspective view of the aseptic vial piercing system of FIG. 1, in accordance with an aspect of the present invention.
Figure 11:
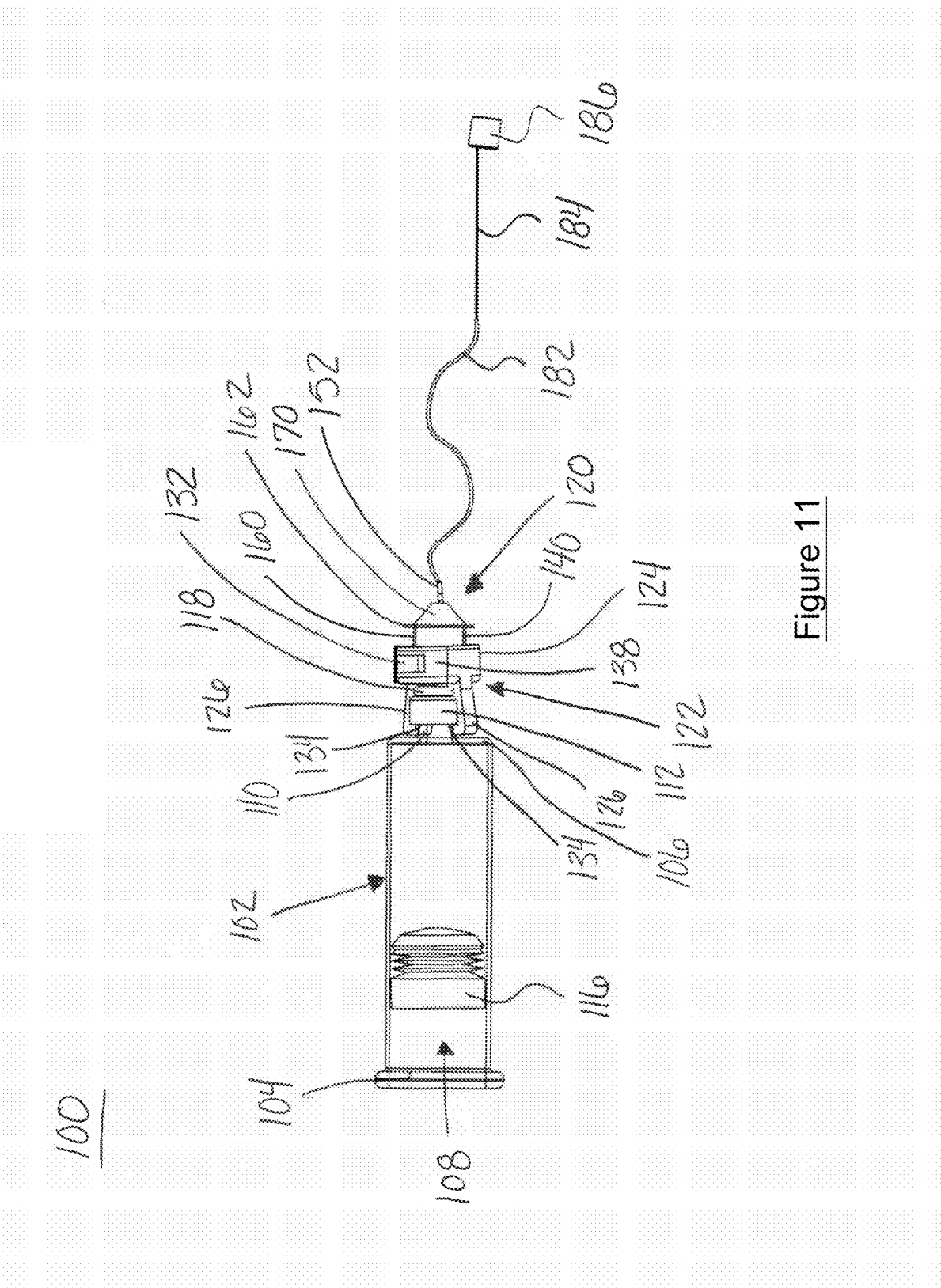
FIG. 11 is a side view of the aseptic vial piercing system of FIG. 10, in accordance with an aspect of the present invention.
Figure 12:
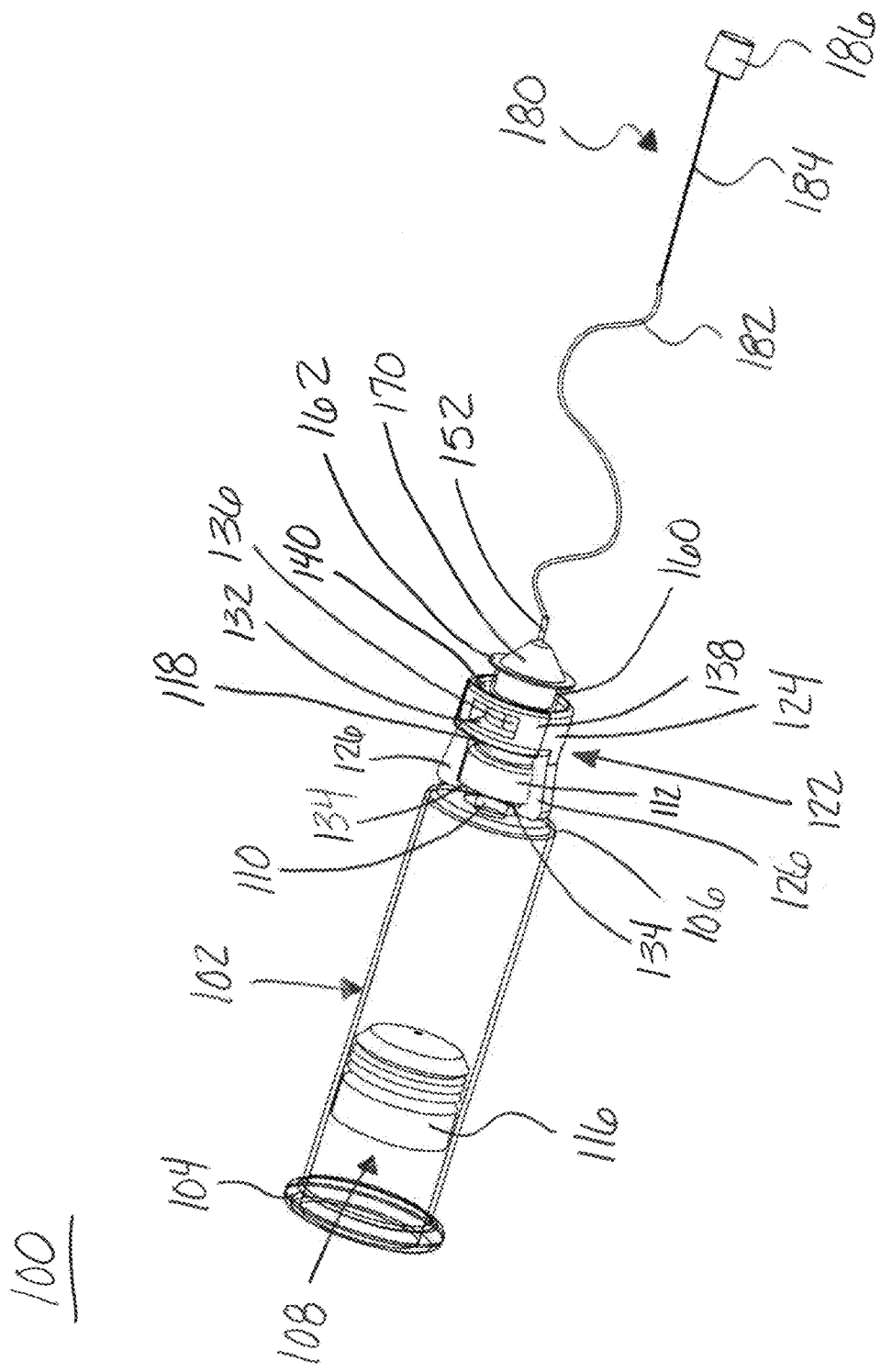
FIG. 12 is a perspective view of the aseptic vial piercing system of FIG. 10, in accordance with an aspect of the present invention.

The aseptic piercing system 100 may also include a connector assembly 120, as shown in FIGS. 1 and 2. The connector assembly 120 may include a connector body 122, a support member 140, a needle cover 150, a flowpath forming member or needle 152 (e.g., a staked needle), a collapsible member 160, a support ring 162, an aseptic seal 164, and an impact cushion 170. The connector body 122 may include a base portion 124 and at least one coupling member 126. The base portion 124 may include an opening 128, a recess 130, and a window 132. The opening 128 may extend along the longitudinal axis of the connector body 122 and from a first end to a second end of the base portion 124. The recess 130 may be positioned at the first end of the base portion 124. The at least one coupling member 126 may be, for example, a ring member (not shown) or at least two bias legs 126. The at least two legs 126 may each include an engagement member 134 for engaging the cap 112 to secure the connector assembly 120 to the primary container or vial 102. The engagement member 134 may be, for example, a protrusion extending inward from the at least two legs 126 towards the center of the connector body 122 and the engagement members 134 may be angled.

The connector assembly 120 may also include at least one sterilization indicator 136 and a window seal 138, as shown in FIGS. 1-7. The sterilization indicators 136 may, for example, tell a user if the connector assembly 120 has been sterilized and is ready for use. The sterilization indicators 136 may be positioned within the opening 128 and positioned such that they are viewable through the window 132. The window seal 138 may be, for example, partially or completely transparent to allow for a user to view within the window 132 and at least a portion of the opening 128 of the base portion 124. The window seal 138 may also close the window 132 to form a sterile environment for the flowpath forming member 152.

The support member 140 may include a base portion 142 and a flange member 146 at a second end of the base portion 142. The flange member 146 may be generally perpendicular to the base portion 142. The support member 140 may also include an opening 144 extending from a first end to the second end. The flange member 146 may be sized to engage the recess 130 in the base portion 124 of the connector body 122. The needle cover 150 may be, for example, sized to fit into the opening 144 in the support member 140. The needle cover 150 may also be, for example, shaped to match the shape of the opening 144, although other shapes that would engage the opening 144 are also contemplated. The flowpath forming member 152 may be partially inserted into the needle cover 150 before injection, as shown in FIGS. 3-9. The flowpath forming member 152 may be sized to extend, for example, through the entire connector assembly 120 to pass through the septum 114 for injection of the medication or fluid from the primary container or vial 102.

With continued reference to FIGS. 1 and 2, the collapsible member 160 may be, for example, cylindrical shaped and sized to engage the support member 140. Alternatively, the collapsible member 160 may be, for example, a cylindrical shaped member with cylindrical accordion like ribs extending along at least a portion of the length of the collapsible member 160. The flowpath forming member 152 may extend through the entire collapsible member 160. The support ring 162 may be coupled to the collapsible member 160. An aseptic seal 164 may be placed around the flowpath forming member 152 where the flowpath forming member 152 extends out of the collapsible member 160 to assist with maintaining a sterile environment within the connector assembly 120. The impact cushion 170 may engage the support ring 162 and the collapsible member 160. The impact cushion 170 may restrict forward motion when the primary container or vial 102 is moved forward, while the flowpath forming member 152 remains stationary, to engage the flowpath forming member 152 and collapse collapsible member 160 to cause the flowpath forming member 152 to pierce the septum 114.

The aseptic piercing system 100 may also include an injection assembly 180, as shown in FIGS. 1-5 and 7-12. The injection assembly 180 may include a tube 182, an injection member 184, and a needle cover 186. The tube 182 may be coupled to the flowpath forming member 152 at a first end and the injection member 184 at a second end. The needle cover 186 may engage the injection member 184 at an end opposite the tube 182. The terms "needle cover," "cap," "cover" and "shield" may be used interchangeably herein as they each refer to a structure used to maintain a sterile field about, and protect the patient and medical professional from accidentally being stuck by, the injection member 184. The injection member 184 may be, for example, a needle, microneedle, cannula, or the like for a subcutaneous injection or a tube, dispensing needle, or the like for topical application to the skin, a patch, or the like.

The aseptic piercing system 100 may be assembled by, for example, inserting at least one sterilization indicator 136 within the opening 128 of the connector body 122. A window seal 138 may be secured to the connector body 122 over the window 132. Next, a support member 140 may be positioned in the recess 130 of the connector body 122. The flowpath forming member 152 may be coupled to the needle cover 150. Then, the coupled flowpath forming member 152 and cover 150 may be inserted in the opening 144 in the support member 140 and positioned in the desired position. The coupled flowpath forming member 152 and cover 150 may also be positioned within the collapsible member 160 that is located around the support member 140. Next, the support ring 162 may be coupled to the collapsible member 160 to secure the coupled flowpath forming member 152 and cover 150 to the connector body 122. An aseptic seal 164 may be positioned where the flowpath forming member 152 extends through the collapsible member 160 to prevent any contamination entering from that opening. The impact cushion 170 may then be positioned over the support ring 162, collapsible member 160, and support member 140. The flowpath forming member 152 may extend through the opening 172 in the impact cushion 170 and be coupled to an injection assembly 180. Next, the first end of a tube 182 may be coupled to the flowpath forming member 152 and the second end of the tube 182 may be coupled to an injection member 184. The injection member 184 may have a cover 186 positioned on the end opposite the coupled tube 182. Once the connector assembly 120 and injection assembly 180 are assembled they may be sterilized. The connector assembly 120 may be sterilized by, for example, gamma sterilization to create a sterilized primary medication passage.

After the connector assembly 120 is sterilized, a seal ring 118 may be positioned on the cap 112 of the primary container or vial 102 and the at least one coupling member 126 may be inserted over the cap 112 to secure the connector assembly 120 to the primary container or vial 102. The primary container or vial 102 may be filled with a medication or fluid for injection into a patient. Next, the primary container or vial 102 and needle environment under the window 132 need to be sterilized. To allow for sterilization under the window seal 138, the window seal 138 may be made of, for example, Tyvek® or other like materials. The primary container or vial 102 and connector assembly 120 may then be sterilized using ethylene oxide (ETO) sterilization. The ETO sterilization may penetrate the window seal 138 to sterilize the vial face at the second end 106 of the primary container or vial 102, the seal ring 118, needle cover 150, and needle area proper 152.

Figure 13:
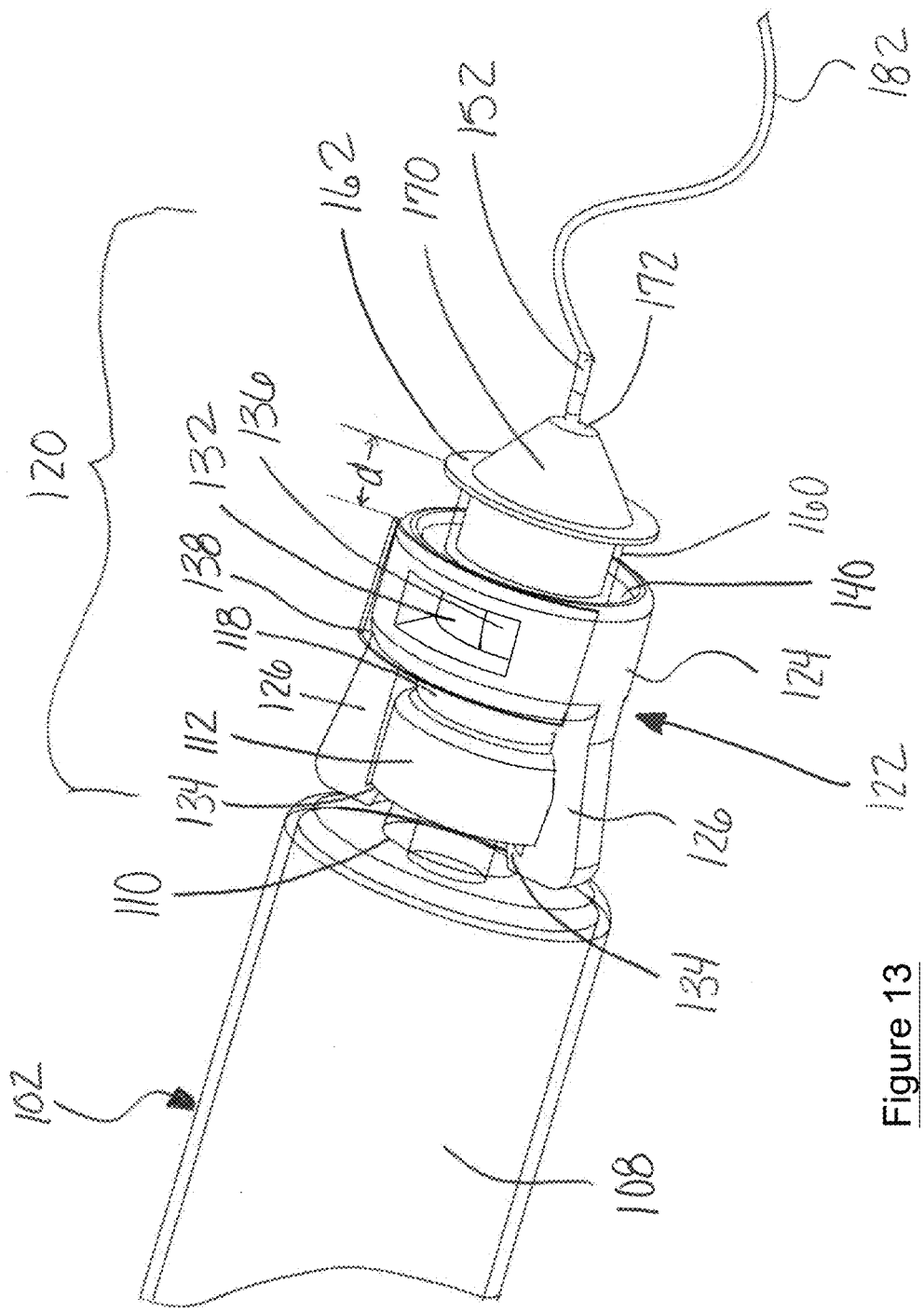
FIG. 13 is an enlarged perspective view of a portion of the aseptic vial piercing system of FIG. 10 showing the collapsible member in a fully extended position, in accordance with an aspect of the present invention.
Figure 14:
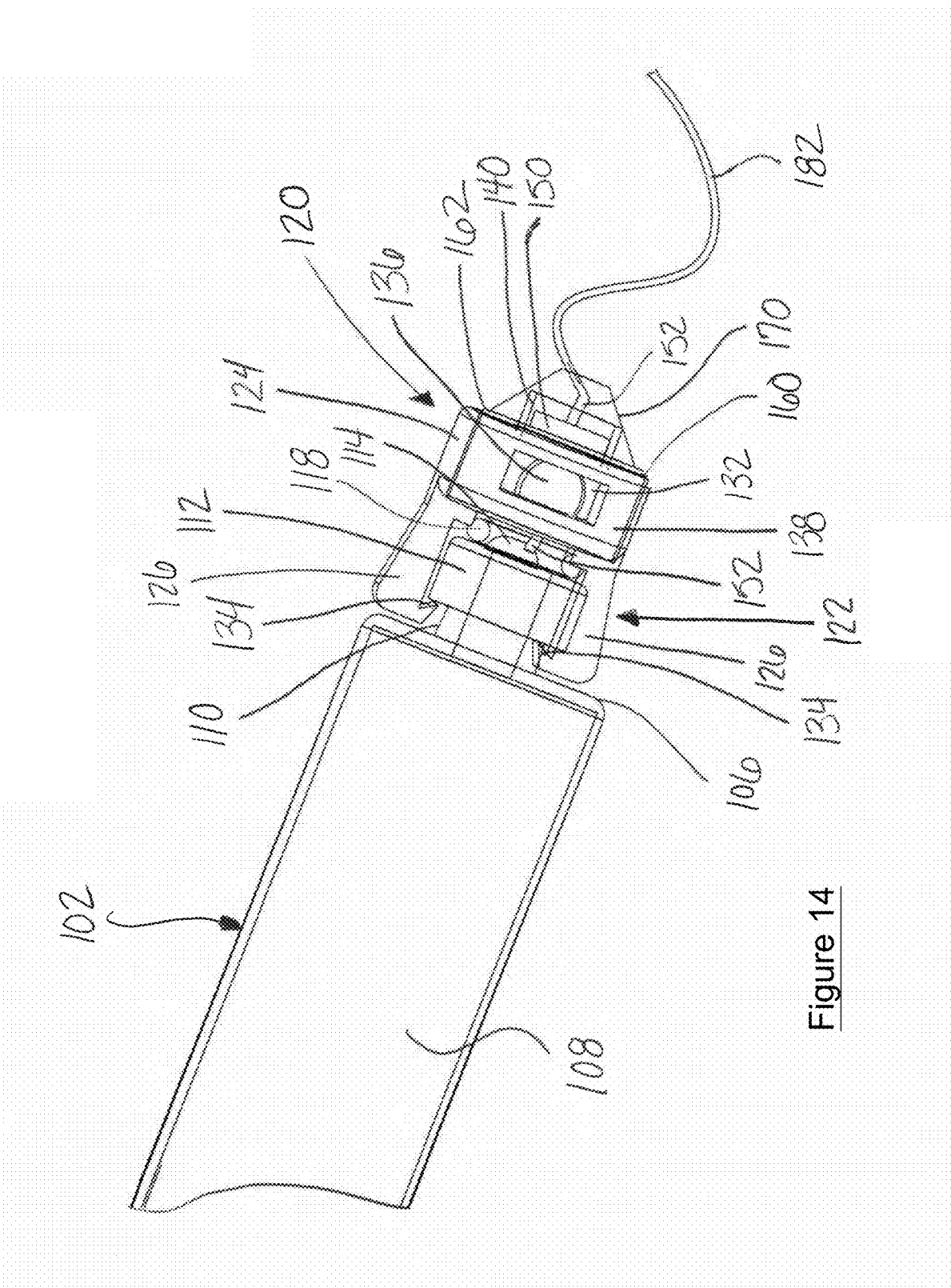
FIG. 14 is an enlarged perspective view of a portion of the aseptic vial piercing system of FIG. 10 showing the collapsible member in a collapsed position, in accordance with an aspect of the present invention.

The method of using the aseptic piercing system 100 may include, for example, viewing the sterilization indicators 136 to confirm that both gamma and ETO sterilization have been performed on the aseptic piercing system 100. If the indicators 136 confirm that sterilization is complete, the cover 186 may be removed from the injection member 184 and coupling the injection member 184 to a patient. The primary container or vial 102 may then be moved forward and the impact cushion 170 may restrict forward movement of the flowpath forming member 152. As the primary container or vial 102 is moved the collapsible member 160 may collapse and with the continued forward motion of the primary container or vial 102 force the flowpath forming member 152 to extend through the fixed cover 150, as shown in FIG. 14. The collapsible member 160 may move for example a distance "d" as shown in FIG. 13. The distance "d" may be, for example, equal to the distance the flowpath forming member 152 needs to be force to pierce the septum 114. Once the staked flowpath forming member 152 penetrates the cover 150 the flowpath forming member 152 will pierce the septum 114 of the primary container or vial 102, as shown in FIG. 14. Once the flowpath forming member 152 passes through the septum 114 into the primary container or vial 102 a fluid connection is formed to enable the medication or fluid within the primary container or vial 102 to flow through the injection assembly 180 and into the patient.

Figure 15:
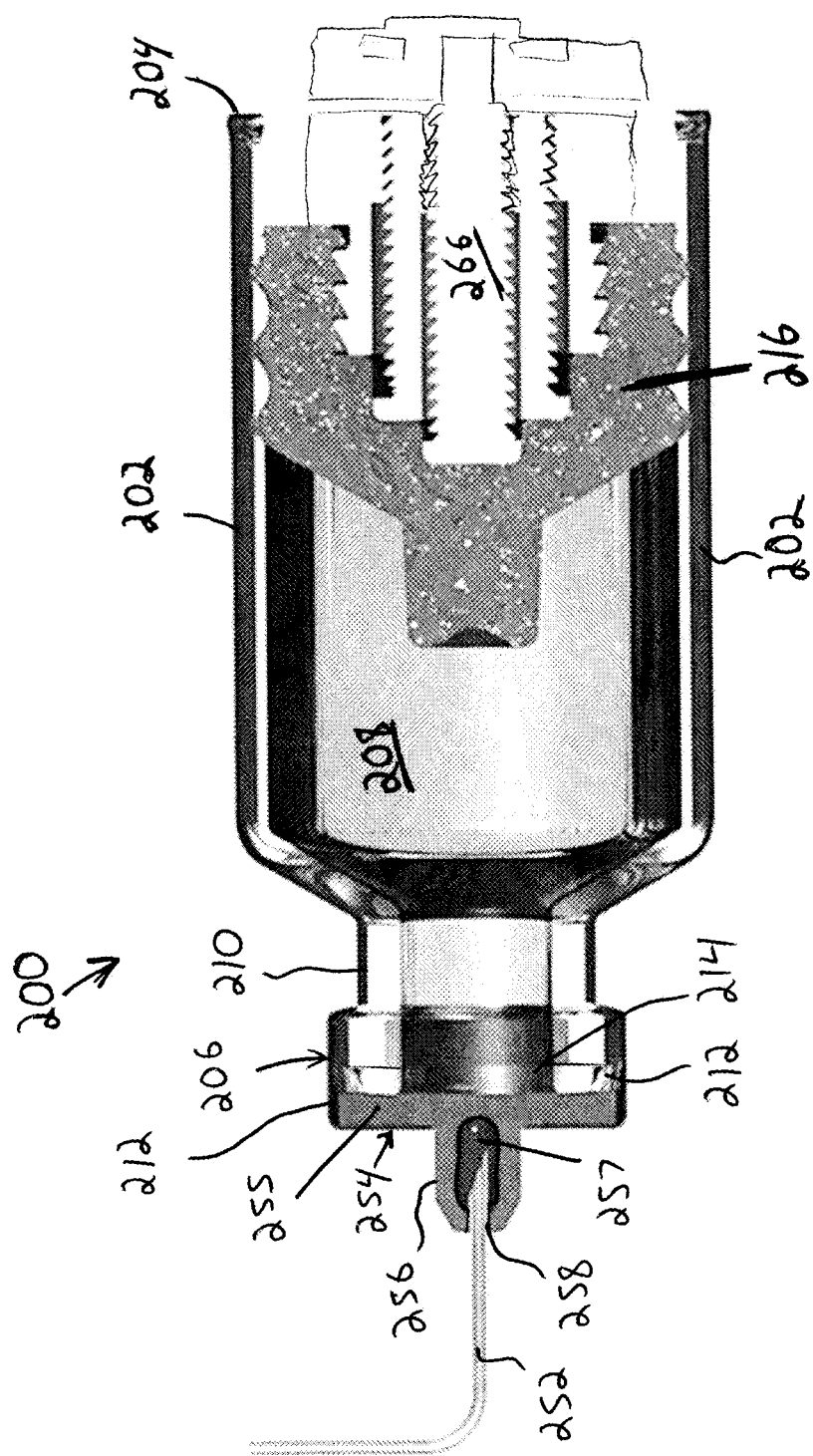
FIG. 15 is an assembled cross-sectional view of an aseptic vial piercing system in a pre-activated state, in accordance with another aspect of the present invention.
Figure 16:
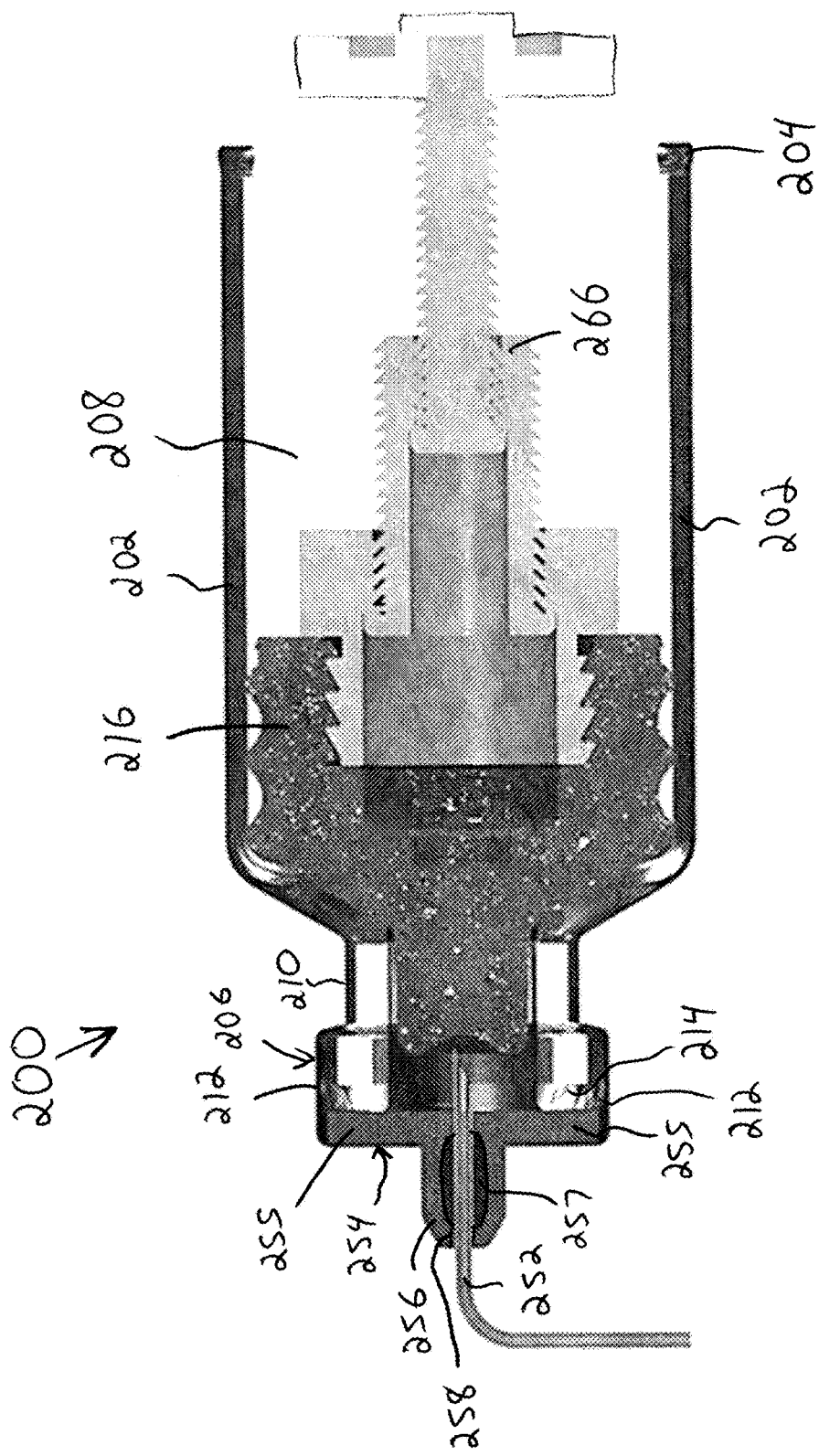
FIG. 16 is an assembled cross-sectional view of the aseptic vial piercing system of FIG. 15 in an activated state with a flowpath forming member aseptically coupled in fluid communication with a primary container, in accordance with another aspect of the present invention.

FIGS. 15 and 16 illustrate an alternative embodiment of an aseptic piercing system generally indicated by reference numeral 200. Aseptic piercing system 200 is similar to the aseptic piercing system 100 described above and illustrated in FIGS. 1-14, and therefore like reference numerals preceded by the numeral "2", as opposed to "1", are used to indicate like functioning elements. As shown in FIG. 15, the primary container or vial 202 may contain a drug, medication or other liquid or liquid like substance in an as-provided or loaded state. The system 200 may be utilized with, or part of, a delivery device that actuates the system to deliver the contents of the primary container 202 to and through the flowpath or flowpath forming member 252 (e.g., a staked needle), and, ultimately, to the patient.

As also shown in FIG. 15, the system 200 may include a piston 216 slidably received within the cavity 208 of the primary container 202 behind the contents such that the contents are positioned between the piston 216 and the second end 206 of the primary container 202 (in the as-provided or loaded state). The piston 216 and the interior of the primary container 202 may form an aseptic or sterile seal that prevents pathogens or other contaminants from passing therebetween and into the contents. The interior of the primary container 202, including the interior surfaces of the primary container 202, the contents, and the interior surfaces of the piston may be sterile or aseptic. The piston 216 may thereby maintain the sterile nature of the interior of the primary container 202. In some embodiments, the piston is made from rubber.

The system 200 may also include a boot or nipple portion 254 positioned at the second end 206 of the primary container 202, as shown in FIG. 15. The boot 254 may include a base portion 255 positioned over (and/or at least partially under) a cap 212 (e.g., a crimp cap) on the opening at the second end 206 of the primary container 202, as described above. As also discussed above, the cap 212 may couple a septum 214 over and/or within the opening at the second end 206 of the primary container 202. As such, the base portion 255 may overlie the septum 214 and the opening of the primary container 202. The assembly of at least the primary container 202, septum 214, cap 212 and boot 254 may be sterilized before assembly with other parts of the system (as described further below) such that at least the interior or non-exposed surfaces thereof (other than the cavity 257 of the boot as explained further below) which the flowpath forming member 252 will pass through, as explained further below, are sterile.

As shown in FIG. 15, the boot portion 254 may include a chamber portion 256 extending from the base portion 255 in a direction at least generally away from the piston 216. The chamber portion 256 defines a cavity or chamber 257, as shown in FIG. 15. The chamber portion 256 includes an opening 258 in communication with the cavity 257, as shown in FIG. 15. In some embodiments, the boot portion 254 may be integrated with the septum 214 (i.e., integral or of one-piece construction). In some alternative embodiments (not shown), the boot 254 may be provided or initially assembled on the flowpath forming member 252 and not installed directly on/with the primary container 202 and/or integrated with the septum 214. For example, the boot 254 may be provided with a subassembly that is separately sterilized from the primary container 202, and assembled with the primary container 202 in a non-sterile environment (and potentially non-destructively sterilized after assembly), as explained further herein with respect to other embodiments.

As also shown in FIG. 15, a portion of the flowpath forming member 252, such as a needle, tube or the like, may extend through the opening 258 of the chamber portion 256 and into the cavity 257 of the boot 254, but not through the base portion 255. A first tip or end portion of the flowpath forming member 252 may thereby be positioned within the cavity 257. The opening 258 may be pre-formed, or the opening 258 may be formed by the penetration of the flowpath forming member 252 through the chamber portion 256. The opening 258 of the chamber portion 256 may form a sterile sliding seal about the flowpath forming member 252 such that pathogens or other contaminants are prevented from passing therebetween and into the cavity 257 and the flowpath forming member 252 can axially translate with respect to the boot portion 254 without disrupting the sterile seal therebetween. The cavity 257 may be sterile or aseptic such that the inner surfaces of the cavity 257 and the first end of the flowpath forming member 252 is positioned therein are sterile. As explained further below with respect to another embodiment, the cavity 257 may initially not be sterile, but may be sterilized after the first end of the flowpath forming member 252 is inserted through the opening 258 and into the cavity 257. In alternative embodiments, rather than the boot 254, a convoluted flexible (e.g., rubber) bellows or bladder member may form the cavity 257 and allow axial translation of the primary container 202 in relation to the first end portion of the flowpath forming member 252 (or vice versa). The flexible member may also seal or form the cavity 254 about the first end portion of the flowpath forming member 252 after sterilization thereof.

The flowpath forming member 252 may be positionally fixed with respect to the primary container 202 and the components fixed thereto. Stated differently, the flowpath forming member 252 may be substantially fixed in space (such as fixed to a device which the system is utilized with), and the primary container 202 and components fixed thereto may be movable or translatable with respect to the flowpath forming member 252 (such as movable or translatable with respect to a device which the system is utilized with). For example, the flowpath forming member 252 may be fixed to a larger device or system to which the primary container 202 is movably attached.

As shown in FIG. 15, the piston 216 may be coupled to a translation mechanism 266 that is configured to axially translate the piston 216 with respect to the primary container 202 (and the components coupled thereto) towards the second end 206. The translation mechanism may be any mechanism effective to selectively axially translate the piston 216 with respect to the primary container 202 (and the components fixed thereto) towards the second end 206. As shown in FIG. 16, axial movement of the piston 216 with respect to the primary container 202 (and the components fixed thereto) causes the piston 216 to act against the contents (e.g., drug, medication). The system 200 design and/or friction of the piston 216 with the primary container 202 allows or dictates that the primary container 202 will move axially more easily than the piston 216 such that the primary container 202 will axially translate first via the translation mechanism 266. As an example, the axial movement of the piston 216 may try to compress the contents of the primary container 202, and, thereby, transfer the axial forces against the second end 206 of the primary container to axially translate the primary container 202 and the components fixed thereto.

As shown in FIG. 16, the translation mechanism 266 may axially translate the piston 216, and thereby the primary container 202 and the components fixed thereto, to such a degree such that the first end portion of the stationary or fixed flowpath forming member 252 pierces and penetrates or extends through the base portion 255 of the boot 254, the septum 214, and the cavity 208 of the primary container 202, and thereby into fluid communication with the contents of the primary container 202. Stated differently, the translation mechanism 266 may axially translate the piston 216, and thereby the primary container 202 and the components fixed thereto, to such a degree such that the base portion 255 of the boot 254 is impaled on the first end portion of the stationary or fixed flowpath forming member 252 such that the flowpath forming member 252 extends through the septum 214 and into the cavity 208 of the primary container 202 and thereby into fluid communication with the contents thereof. In some embodiments, the system 200 may be configured such that, after activation, no more of the flowpath forming member 252 than the portion thereof that was positioned within the sterile cavity 257 of the chamber portion 256 pre-activation extends into the cavity 208 of the primary container 202. Axial movement of the primary container 202 via the piston 216 and axial translation mechanism 266 thereby effectuates sterile coupling of the flowpath forming member 252 with the cavity 208 of the primary container 202 (and the contents therein). This leaves the primary container 202 intact until use, giving the contents within the cavity 208 of the primary container 202 better stability in storage and prevents leak out the flowpath forming member 252 before use.

Once the first end portion of the flowpath forming member 252 extends into the cavity 208 of the primary container 202 and, thereby into fluid communication with the contents thereof, further axial translation of the primary container 202 and the components fixed thereto via the translation mechanism 266 may be prevented. For example, the device or system into which the system 200 is installed may include a stop configured to only allow limited axial translation of the primary container 202. As such, as shown in FIG. 16, further axial translation of the piston 216 via the translation mechanism 266 after the first end portion of the flowpath forming member 252 extends into the cavity 208 of the primary container 202 and thereby into fluid communication with the contents thereof forces the contents within the primary container 202 through the flowpath formed by the flowpath forming member 252. As noted above, the flowpath forming member 252 may be configured to, ultimately, deliver the contents to a patient as a subcutaneous injection or topical application, for example.

The translation mechanism 266 may effectuate or accomplish axial motion of the piston 216, and thereby axial translation of the primary container 202 and pumping of the contents of the cavity 208 through the flowpath forming member 252, via any mode or method. For example, the exemplary embodiment illustrated in FIGS. 15 and 16 includes a leadscrew mechanism coupled to the back side of the piston 216 that extends axially upon relative rotation about the axis. The base of the leadscrew mechanism may be positionally fixed or stationary to effectuate movement of the piston 216. In another exemplary embodiment (not shown), the translation mechanism 266 may include a manually engageable surface or member that is manually manipulated by a user to axially translate the piston 216. For example, the system 200 may include a cartridge or a plunger coupled to the back side of the piston 216 that is manually engaged and axially translated to axially translate the piston 216. In another exemplary embodiment (not shown), the translation mechanism 266 may include a pneumatic or hydraulic drive member that is actuated or initiated by a user that provides for axial translation of the primary container 202 and axial translation of the piston 216 with respect to the primary container 202. The pneumatic or hydraulic drive member may utilize pneumatic or hydraulic forces to axially translate the drive member. The drive member may be in the form of expanding bellows, an expanding bladder, an expanding diaphragm or a sliding seal or piston, for example. The drive member may allow for or provide the axial translation of the primary container 202, and the direct pneumatic or hydraulic pressure may axial translation the piston 216.

Figure 17:
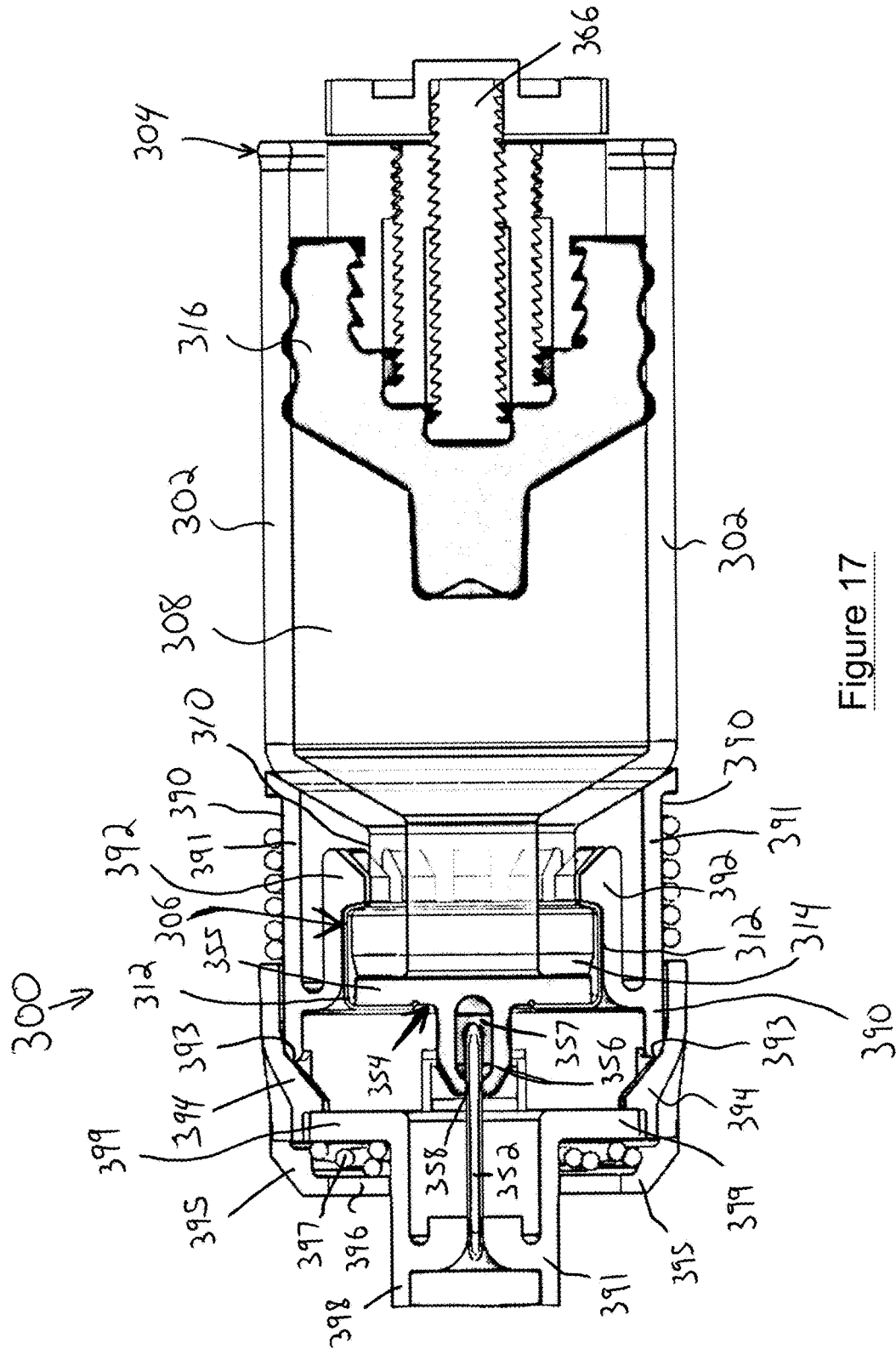
FIG. 17 is an assembled cross-sectional view of an aseptic vial piercing system in a pre-activated state, in accordance with another aspect of the present invention.

FIGS. 17-20 illustrate an exemplary alternative embodiment of an aseptic piercing system generally indicated by reference numeral 300. Exemplary aseptic piercing system 300 is similar to the exemplary aseptic piercing system 100 described above and illustrated in FIGS. 1-14 and the exemplary aseptic piercing system 200 described above and illustrated in FIGS. 15 and 16, and therefore like reference numerals preceded by the numeral "3", as opposed to "1" or "2", are used to indicate like functioning elements. As shown in FIG. 17, the configuration of the primary container 302, the contents therein, the piston 316, the translation mechanism 366, the cap 312, the septum 314, and the boot 354 of the aseptic piercing system 300 may be substantially the same as that of the aseptic piercing system 200 described above and illustrated in FIGS. 15 and 16. The aseptic piercing system 300 of FIGS. 17 and 18 may differ from the aseptic piercing system 200 of FIGS. 15 and 16 in the mode of sterile coupling the flowpath forming member 352 with the cavity 308 of the primary container 302.

Figure 18:
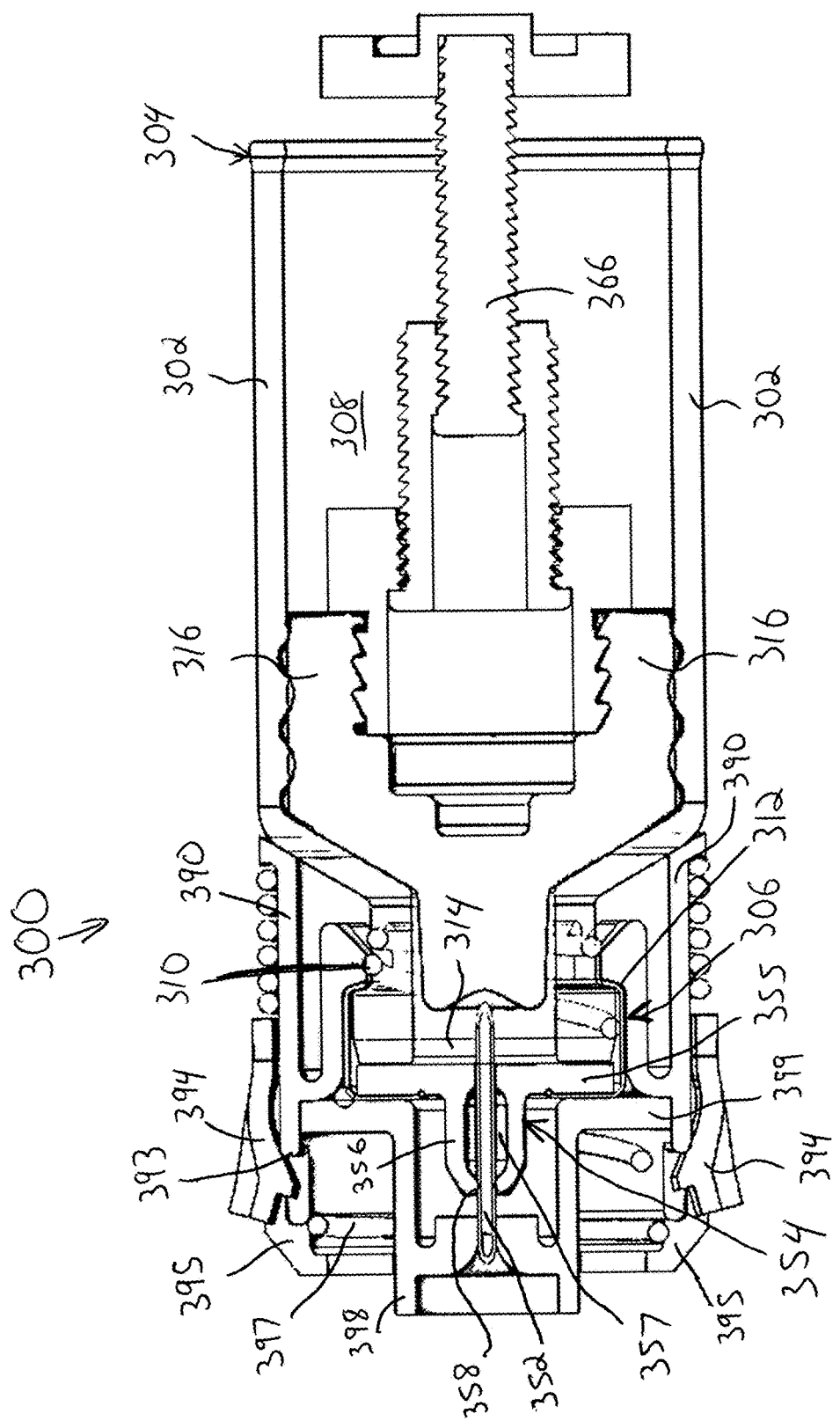
FIG. 18 is an assembled cross-sectional view of the aseptic vial piercing system of FIG. 17 in an activated state with a flowpath forming member aseptically coupled in fluid communication with a primary container, in accordance with another aspect of the present invention.

As shown in FIGS. 17 and 18, rather than impaling the base portion 355 of the boot 354 and the septum 314 into and through the end portion of the flowpath forming member 353 (i.e., translating the primary container 302 with respect to the stationary or fixed flowpath forming member 353) as described above with respect to the aseptic piercing system 200 of FIGS. 15 and 16, the aseptic piercing system 300 drives the end portion of the flowpath forming member 353 into and through the base portion 355 of the boot 354 and the septum 314 and into the cavity 308 of the primary container 302 and thereby into fluid communication of the contents therein (i.e., translating the flowpath forming member 353 with respect to the stationary or fixed primary container 302).

As shown in FIGS. 17 and 18, the aseptic piercing system 300 includes a collar 390 coupled or fixed to the second end 306 of the primary container 302. The collar 390 may include a plurality of circumferentially spaced fingers 392 engaging and surrounding the neck region 310 of the primary container 302. In this way, the collar may be fixed to the second end 306 of the primary container 302. However, the collar 390 may be otherwise coupled to the second end 306 of the primary container 302. The collar 390 may include an axially extended wall portion 391 that extends at least partially about the neck region 310, the opening of the second end 306, the cap 312, the septum 314 and/or the boot 354. The wall portion 391 of the collar 390 may be positioned radially or laterally outward of the neck region 310 and/or extend axially past the neck region 310, cap 312 and septum 314. The wall portion 391 of the collar 390 may also extend axially past at least a portion of the boot 354, such as past the base portion 355 and partially past the chamber portion 356, as shown in FIGS. 17 and 18.

In the pre-activated state of the system 300 as shown in FIG. 17, at least one engagement portion or distal axial edge 393 of the collar 390 may engage a corresponding at least one radially or laterally inwardly extending cam, latch or actuation portion 394 of a driver retainer member 395. The retainer member 395 may be axially slidably or translatably coupled to the collar 390. The collar 390 and retainer member 395 may be configured such that in the pre-activated state or arrangement shown in FIG. 17, at least a portion of the cam or actuation portion 394 of the retainer member 395 is positioned axially directly behind a retaining portion 399 of a driver member 398 axially slidably or translatably coupled within the retainer member 395. As shown in FIG. 17, a flowpath engaging portion 391 of the driver member 398 may extend axially into and through an axial end cap portion 396 of the retainer member 395 and into an interior portion of the retainer member 395, and the retaining portion 399 of the driver member 398 may extend from the flowpath engaging portion 391. In some embodiments, the flowpath engaging portion 391 of the driver member 398 may be substantially cylindrical and the retaining portion 399 of the driver member 398 may be a flange extending about an axial end of the flowpath engaging portion 391, as shown in FIG. 17.

As also shown in FIG. 17, in the pre-activated state of the system 300 an elastically deformed biasing or resilient member 397 may be positioned axially between the cap portion 396 of the retainer member 395 and the retaining portion 399 of a driver member 398. The biasing member 397 may thereby exert a preloaded axial force against the driver member 398 in the pre-activated state of the system 300 acting in the direction towards the primary container 302. The biasing member 397 may be any member effective in applying the axial preloaded force in the pre-activate state, and then releasing such preloaded force upon activation, as discussed below with reference to FIG. 18. In some embodiments, the biasing member 397 may be a spring.

The flowpath forming member 352 may be fixed or coupled to the driver member 398 such that the flowpath forming member 352 axially slides or translates with the driver member 398. As discussed above, in the pre-activated state of the system 300 the first end portion of the flowpath forming member 352 may be positioned within the sterile cavity 357 of the chamber portion 356 of the boot 354, but not through the base portion 355 of the boot 354, the septum 314 and/or into the cavity 308 of the primary container. As shown in FIG. 17, the first end portion of the flowpath forming member 352 may be axially spaced from the base portion 355 of the boot 354 in the pre-activated state.

The assembly of the driver member 398, flowpath forming member 352, biasing member 397 and driver retainer member 395 may be axially fixed during the pre-activation state of the system 300 and upon activation prior to release of the driver 398, as explained further below. Stated differently, the driver member 398, flowpath forming member 352, biasing member 397 and driver retainer member 395 may be substantially axially fixed in space (such as fixed to a device with which the system 300 is utilized), and the primary container 302 and components fixed thereto may be axially movable or translatable with respect to the driver member 398, flowpath forming member 352, biasing member 397 and driver retainer member 395 (such as movable or translatable with respect to a device with which the system is utilized) during the pre-activation state of the system 300 and upon activation prior to release of the driver 398. For example, the driver member 398, flowpath forming member 352, biasing member 397 and driver retainer member 395 may be axially fixed to a larger device or system to which the primary container 302 (and the components fixed thereto) is movably attached.

When the system 300 is activated as shown in FIG. 18 (and in comparison to FIG. 17), the translation mechanism 366 may be initiated or activated (as discussed above) to axially translate the piston 316 towards the second end 306 of the primary container 302. As discussed above, such axial movement of the piston 316 within the cavity 308 of the primary container 302 will act to compress the contents within the cavity 308 and, ultimately, axially translate the primary container 302 and the components fixed thereto in an axial direction extending from the first end 304 to the second end 306. Upon activation of the system 300 as shown in FIG. 18, the translation mechanism 366 may axially translate the primary container 302 to such an extent that the at least one engagement portion 393 of the collar 390 engages and radially or laterally deflects or translates the at least one cam or actuation portion 394 of the driver retainer member 395 out from axially behind the retaining portion 399 of the driver member 398. In this way, the retaining portion 399 of the driver member 398 is then able to clear the at least one cam or actuation portion 394 of the driver retainer member 395 and allow the preloaded force of the biasing member 397 to axially translate the driver 398, and the flowpath forming member 352 fixed thereto, towards the second end 306 of the primary container 302.

It is noted that the system 300 may be configured such that the axial translation of the primary container 302 and collar 390 to release the at least one cam or actuation portion 394 may not act to cause the first end portion of the flowpath forming member 352 to pierce and/or extend through the base portion 355 of the boot 354 and/or the septum 314. For example, in the pre-activated state the first end portion of the flowpath forming member 352 may be sufficiently axially spaced from the base portion 355 of the boot 354 and/or the septum 314 such that the axial translation of the primary container 302 and collar 390 to release the at least one cam or actuation portion 394 does not act to cause the first end portion of the flowpath forming member 352 to pierce and/or extend through the base portion 355 of the boot 354 and/or the septum 314.

As shown in FIG. 18, axial translation of the driver 398 and the flowpath forming member 352 toward the second end 306 of the primary container 302 causes the first end portion of the flowpath forming member 352 to pierce and penetrate or extend through the base portion 355 of the boot 354, the septum 314, and the cavity 308 of the primary container 302, and thereby into fluid communication with the contents of the primary container 302. Stated differently, the translation mechanism 366 may axially translate the piston 316, and thereby the primary container 302 and the components fixed thereto such as the collar 390, to such a degree such that driver 398 is "released" and impales the boot 354 and septum such that the flowpath forming member 352 extends into the cavity 308 of the primary container 302 and thereby into fluid communication with the contents thereof. In some embodiments, the system 300 may be configured such that, after activation, no more of the flowpath forming member 352 than the portion thereof that was positioned within the sterile cavity 357 of the chamber portion 356 pre-activation extends into the cavity 308 of the primary container 302. Axial movement of the driver 398 and flowpath forming member 352 thereby effectuates sterile coupling of the flowpath forming member 352 with the cavity 308 of the primary container 302 (and the contents therein). This leaves the primary container 302 intact until use, giving the contents within the cavity 308 of the primary container 302 better stability in storage and prevents leaks out the flowpath forming member 352 before use.

The biasing member 397 may be configured such that the flowpath forming member 352 impales the boot 354 and/or septum 314 at a substantially high speed, such as at least about 10 mm/sec. In some embodiments, the biasing member may be configured such that the flowpath forming member 352 impales the boot 354 and/or septum 314 at about 40 mm/sec. The relatively quick piercing of the boot 354 and/or septum 314 via the biasing member 397 may advantageously prevent leakage of the contents of the cavity 308 which may be under pressure via the piston 316 while the flowpath forming member 352 is partially penetrated.

Once at least one cam 394 is released and the first end portion of the flowpath forming member 352 extends into the cavity 308 of the primary container 302, and thereby into fluid communication with the contents thereof, further axial translation of the primary container 302 and the components fixed thereto via the translation mechanism 366 may be prevented. As such, as shown in FIG. 17, further axial translation of the piston 316 via the translation mechanism 366 after the first end portion of the flowpath forming member 352 extends into the cavity 308 of the primary container 302 and, thereby into fluid communication with the contents thereof forces the contents through the flowpath formed by the flowpath forming member 352. As noted above, the flowpath forming member 352 may be configured to, ultimately, deliver the contents to a patient as a subcutaneous injection or topical application, for example.

Figure 19:
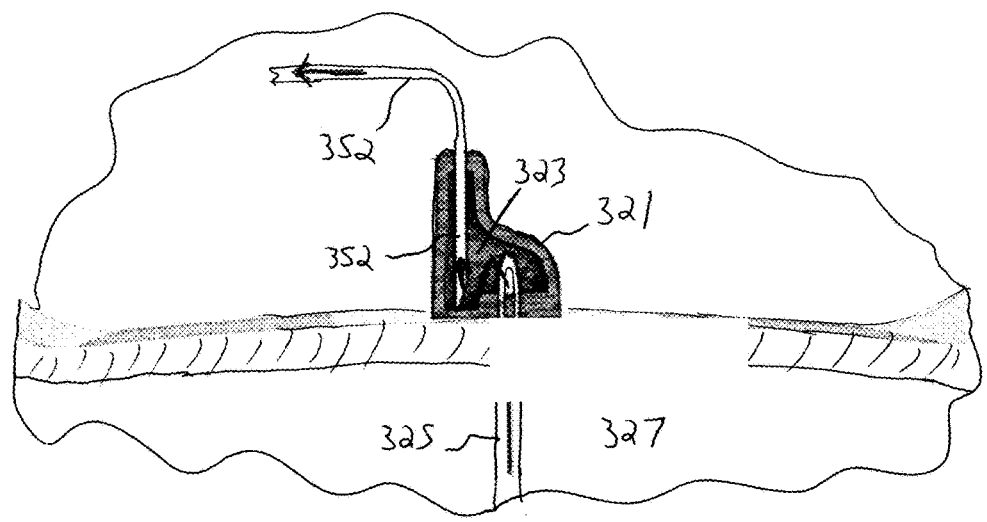
FIG. 19 illustrates introduction of a sterilent into the flowpath forming member of the aseptic vial piercing system of FIG. 17 after non-sterile assembly thereof.
Figure 20:
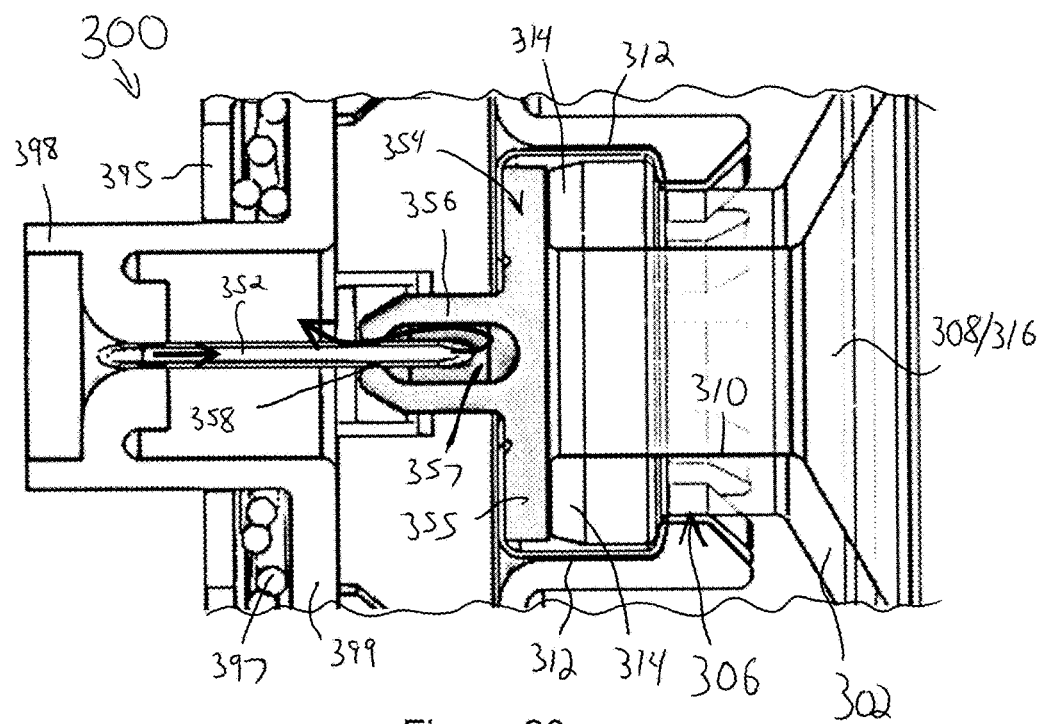
FIG. 20 illustrates sterilization of the end portion of the flowpath forming member and the cavity of the boot member of the assembled aseptic vial piercing system of FIG. 17 via the sterilent.

FIGS. 19 and 20 illustrate systems and methods for sterilizing the cavity 357 of the chamber portion 356 of the boot 354 and the first end or tip portion of the flowpath forming member 352. In some embodiments, the boot 354 may initially be coupled to the primary container 302 in an unsterile state. Similarly, the first end portion of the flowpath forming member 352 may be inserted into the cavity 357 in an unsterile state when the system 300 is initially assembled, as shown in FIG. 17 for example. In such a configuration of the system 300, a sterilant, such as a gaseous sterilant, may be injected through the pathway of the flowpath forming member 352 and out of the first end portion into the cavity 357. In this way, the pathway of the flowpath forming member 352, the exterior surface of the first end portion of the flowpath forming member 352 within the cavity 357, and the cavity 357 itself may be sterilized in an assembled state of the system 300. The sterilent may be any sterilent effective to sterilize the flowpath forming member 352, the exterior surface of the first end portion of the flowpath forming member 352 within the cavity 357, and the cavity 357. For example, the sterilent may be ethylene-oxide gas (EtO), vaporized hydrogen peroxide (VHP), nitrogen dioxide (NO2), chlorine dioxide (ClO2), or combinations thereof.

As shown in FIG. 19, the sterlient may be introduced into the flowpath forming member 352 via a second end portion of the flowpath forming member 352. The second end portion of the flowpath forming member 352 may extend into a seal 321 defining a cavity 323. The seal 321 may be positioned adjacent an exterior wall or portion 327 of the system 300 or a system or device in which the system 300 is utilized or installed. In this way, as shown in FIG. 19, a needle or other insertion member 325 may be utilized to extend through the exterior wall 327 and the seal 321 and into the cavity 323. The seal 321 may be substantially airtight but for the flowpath forming member 352 and the insertion member 325. In this way, the sterilent may be introduced into the cavity 323 via the insertion member 325, and therefrom into the flowpath forming member 352, as shown by the arrows in FIG. 19. The seal 321 may be configured to seal any apertures caused by the insertion member 325 and/or the flowpath forming member 352 after the sterilent is introduced.

As illustrated in FIG. 20, the sterilent may flow through the flowpath forming member 352 from the second end to the first end and into the cavity 357 of the chamber portion 256 of the boot 354. The chamber portion 356 may be configured to vent positive pressure out of the opening 358 about the first end portion of the flowpath forming member 352 to allow the sterilient to flush out the atmosphere inside the flowpath forming member 352 and within the cavity 357, as shown by the arrows in FIG. 20. The flowpath formed by the flowpath forming member 352, the exterior surfaces of the first portion of the flowpath forming member 352 within the cavity 357, and the cavity 3527 itself may thereby be sterilized after the system 300 is assembled. After sterilization, the sterilent within the flowpath forming member 352 and the cavity 357 may be flushed with an inert gas (e.g., nitrogen) to prevent damage to the contents of the primary container 302 in the same manner as the sterilent was introduced and utilized to flush and sterilize the non-sterile atmosphere within the flowpath forming member 352 and the cavity 357.

Figure 23:
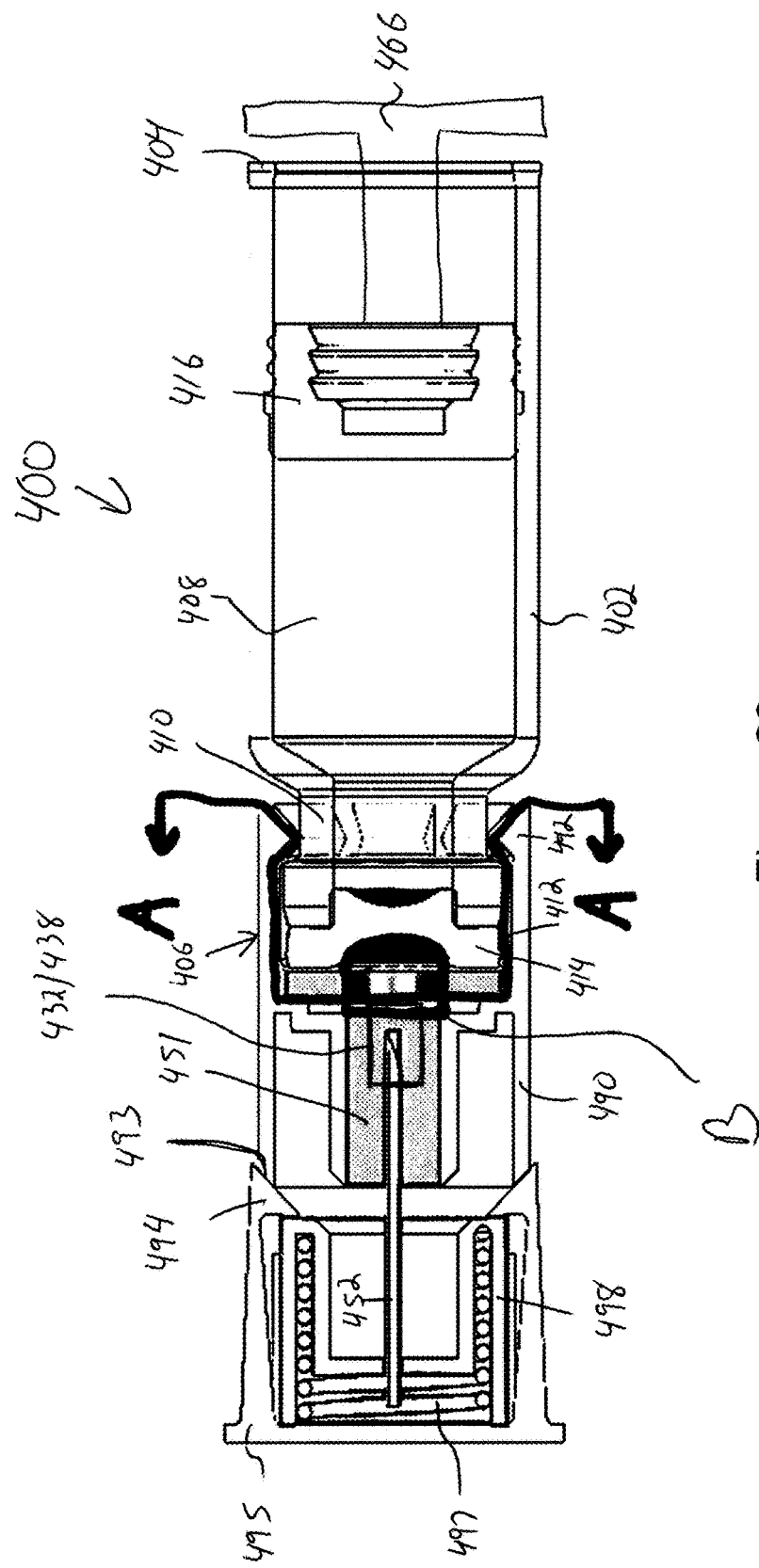
FIG. 23 illustrates sterile and non-sterile portions of the aseptic vial piercing system of FIG. 21 and potential post-assembly sterilization of the non-sterile portions.

FIGS. 21-23 illustrate an exemplary alternative embodiment of an aseptic piercing system generally indicated by reference numeral 400. Exemplary aseptic piercing system 400 is similar to the exemplary aseptic piercing system 100 described above and illustrated in FIGS. 1-14, the exemplary aseptic piercing system 200 described above and illustrated in FIGS. 15 and 16, and the exemplary aseptic piercing system 300 described above and illustrated in FIGS. 17-20, and therefore like reference numerals preceded by the numeral "4", as opposed to "1," "2" or "3," are used to indicate like functioning elements.

As shown in the pre-activate state in FIG. 21 and the activated state in FIG. 22, the system 400 may utilize a similar primary container 402 piercing configuration as the aseptic piercing system 300 described above and illustrated in FIGS. 17-20 in that the flowpath forming member 452 is driven into and through the septum 414 and into the cavity 408 of the primary container 402 and into fluid communication with the contents therein. One difference between the system 400 and the system 300 is that the at least one latch or cam portion 494 is a portion of the driver retainer member 495 rather than the collar 490, as shown in FIGS. 21 and 22.

As shown in FIG. 21, the system 400 further differs from the system 300 in that the system 400 does not include a boot member that includes a chamber portion that forms a cavity for housing the first end portion of the flowpath forming member 452 in the pre-activated state of the system 300. Rather, the system 400 includes a plug 451 in which the first end portion of the flowpath forming member 452 is positioned in the pre-activated state, as shown in FIG. 21. The plug member 451 may provide an aseptic seal about the first end portion of the flowpath forming member 452. In some embodiments, prior to being assembled with the primary container 402, at least the plug 451 and the first end portion of the flowpath forming member 452 therein may be sterilized (e.g., subjected to radiation) such that the first end portion of the flowpath forming member 452 is sterile and the plug 451 maintains such sterility. In some embodiments, the plug 451 may be rubber.

Upon activation, the translation mechanism 466 may translate the primary container 402 and the collar 490 such that the at least one activation portion 493 biases the at least one latch 494 of the driver retainer 495 to allow the biasing member 497 to drive the driver 498 and the flowpath forming member 452 towards the second end 406 of the primary container 402. While being driven towards the second end 406 of the primary container 402, the plug 451 on the first end portion of the flowpath forming member 452 may come into contact with a portion of the collar 490, the cap 412, the septum 414 and/or another component coupled or proximate to the second end 406 of the primary container 402 such that further axial translation of the plug 451 is prevented. Once further axial translation of the plug 451 is prevented, the flowpath forming member 452 may be further axially translated towards the second end 406 of the primary container 402 such that the first end portion of the flowpath forming member 452 is driven through the plug 451 and into and through the septum 414 and into the cavity 408 of the primary container 402 and, thereby into fluid communication of the contents therein.

As illustrated in FIG. 23, the system 400 provides for be partial sterilization before assembly, non-aseptically assembly, and post-assembly sterilization that does not negatively affect the contents of the primary container 402. For example, the components forming group or subassembly A, such as the driver retainer 495, the resilient member 497, the driver 498, the first end portion of the flowpath forming member 452, the plug 451 and/or the collar 490 may be assembled and sterilized as a unit before being assembled with the primary container 402 and the component fixed thereto. For example, subassembly A may be subjected to gamma ray or other sterilization techniques that would not be acceptable in the presence of the contents of the primary container 402. As noted above, the plug 451 may maintain the sterilization of the first end portion of the flowpath forming member 452. The second end of the flowpath forming member 452 may similarly include a plug member to ensure complete sterilization of the pathway of the flowpath forming member 452 and/or the first and second end portions of the flowpath forming member 452.

As described above, the primary container 402 may be sterilized such that the contents and cavity 408 are aseptic. As such, sterile subassembly A can be coupled to the primary container 402 via the neck region 410 and the collar 490 in a non-sterile environment with affecting the sterility of the first end portion of the flowpath forming member 452, as shown in FIG. 23. However, after assembly of the subassembly A and the primary container 402, the interstitial space B between the primary container 402 and the plug 451 or first end portion of the flowpath forming member 452 may be unsterile, as illustrated in FIG. 23.

To sterilize the interstitial space B, the system 400 may include a window 432 and window seal 438, as shown in FIG. 23. For example, as described above with respect to the system 100 of FIGS. 1-14, the window seal 438 may be a permeable material (e.g., Tyvek fabric) that allows a sterilent (e.g., a sterilizing gas, such as EtO or VHP) to diffuse through the window seal 438 and enter the interstitial space B to sterilize the interstitial space B. The permeability of the window seal 438 may be so small that pathogens (e.g., viruses, etc.) are unable to enter the interstitial space B after sterilization. As another example, the window seal 438 may be transparent or translucent such that UV light is able to penetrate through the window seal 438 and into the interstitial space B to sterilize the interstitial space B.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

We claim:

1. An injection device, comprising:
   a container enclosing a fluid, the container having a first end and a second end;
   a conduit movable between a retracted configuration and a deployed configuration, wherein the conduit is not in fluid communication with the fluid enclosed in the container while in the retracted configuration, and is in fluid communication with the fluid enclosed in the container and configured to deliver the fluid from the container to a patient when in the deployed configuration;
   a piston configured to move from the first end of the container toward the second end of the container;
   a drive member configured to drive the piston; and
   a lock configured to maintain the conduit in the retracted configuration, wherein an application of a force from the drive member to the piston is configured to move the lock and allow the conduit to move into fluid communication with the fluid enclosed in the container.

2. The injection device of claim 1, further including a seal enclosing an opening at the second end of the container.

3. The injection device of claim 2, wherein a portion of the seal directly contacts the fluid enclosed by the container and, in the retracted configuration, a piercing end of the conduit is enclosed by the seal.

4. The injection device of claim 3, wherein, while the conduit is in the deployed configuration, the only portion of the conduit extending into the container includes a portion of the piercing end that was previously enclosed by the seal while the conduit was in the retracted configuration.

5. The injection device of claim 3, wherein, while the conduit is in the retracted configuration, the piercing end of the conduit is configured to be sterilized while being enclosed by the seal.

6. The injection device of claim 3, wherein, during a transition from the retracted configuration to the deployed configuration, the piercing end of the conduit extends through the end of the seal that directly contacts the fluid enclosed by the container.

7. The injection device of claim 1, further including:
   an expandable element having a compressed configuration and an expanded configuration, wherein the expandable element is in the compressed configuration when the conduit is in the retracted configuration, wherein the lock is configured to maintain the expandable element in the compressed configuration while the lock is in a first position, and, when the lock is moved radially outward from the first position, the expandable element is configured to move from the compressed configuration to the expanded configuration.

8. The injection device of claim 7, wherein movement of the expandable element from the compressed configuration to the expanded configuration moves the conduit toward the first end of the container, through the seal, and into fluid communication with the fluid enclosed in the container.

9. The injection device of claim 7, wherein the movement of the expandable element from the compressed configuration to the expanded configuration moves the conduit toward the first end of the container at a speed of at least 10 mm/second.

10. The injection device of claim 7, wherein the expandable element is a spring.

11. The injection device of claim 7, wherein, while the conduit is in the retracted configuration, the conduit is fixed relative to a reference location, and the container is movable relative to the conduit and to the reference location.

12. The injection device of claim 11, wherein after the lock is moved radially outward from the first position, the conduit moves relative to the reference location, and the container is fixed relative to the reference location.

13. The injection device of claim 1, wherein, while the conduit is in the retracted configuration, application of force on the piston along a vector extending from the first end of the container toward the second end of the container moves the container along the vector.

14. The injection device of claim 13, wherein, after the conduit is in the deployed configuration, application of force on the piston along the vector urges the fluid in the container through the conduit.

15. The injection device of claim 1, wherein the piston is configured to seal the first end of the container.

16. An injection device, comprising:
- a container configured to enclose a fluid, the container having a first end, a second end, and a movable piston disposed therein;
- a conduit movable between a retracted configuration and a deployed configuration;
- a drive member configured to drive the piston;
- an expandable element having a compressed configuration and an expanded configuration, the expandable element being coupled to the conduit, wherein the expandable element is in the compressed configuration when the conduit is in the retracted configuration; and
- a lock configured to maintain the expandable element in the compressed configuration while the lock is in a first position, wherein an application of a force from the drive member to the piston is configured to move the lock from the first position, allowing the expandable element to move from the compressed configuration to the expanded configuration and drive the conduit into fluid communication with the fluid enclosed in the container.

17. The injection device of claim 16, wherein the lock prevents expansion of the expandable element while in the first position by impeding a pathway of the expandable element, and an application of force from the drive member moves the lock radially outward from the first position and out of the pathway.

18. The injection device of claim 16, wherein movement of the expandable element from the compressed configuration to the expanded configuration moves the conduit toward the first end of the container at a speed of at least 10 mm/second.

19. An injection device, comprising:
- a container configured to enclose a fluid, the container having a first end and a second end;
- a seal enclosing an opening at the second end of the container;
- a conduit movable between a retracted configuration and a deployed configuration;
- an expandable element having a compressed configuration and an expanded configuration, the expandable element being coupled to the conduit, wherein the expandable element is in the compressed configuration when the conduit is in the retracted configuration, and movement of the expandable element from the compressed configuration to the expanded configuration drives the conduit through the seal into the deployed configuration; and
- a piston configured to move from the first end of the container toward the second end of the container; and
- a drive member configured to drive the piston.

20. The injection device of claim 19, further including a lock configured to maintain the expandable element in the compressed configuration while the lock is in a first position, wherein an application of a force from the drive member to the piston is configured to move the lock from the first position, allowing the expandable element to move from the compressed configuration to the expanded configuration.

21. The injection device of claim 20, wherein the lock prevents expansion of the expandable element while in the first position by impeding a pathway of the expandable element, and the application of force from the drive member moves the lock radially outward from the first position and out of the pathway.

22. The injection device of claim 19, wherein the expandable element is a spring.

* * * * *